(12) United States Patent
Alizad et al.

(10) Patent No.: US 11,213,278 B2
(45) Date of Patent: Jan. 4, 2022

(54) SYSTEM AND METHOD FOR VISUALIZATION OF TISSUE MICROVASCULAR USING ULTRASOUND

(71) Applicant: Mayo Foundation for Medical Education and Research, Rochester, MN (US)

(72) Inventors: Azra Alizad, Rochester, MN (US); Mahdi Bayat, Cleveland, OH (US); Mostafa Fatemi, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 224 days.

(21) Appl. No.: 16/614,474

(22) PCT Filed: May 21, 2018

(86) PCT No.: PCT/US2018/033723
§ 371 (c)(1),
(2) Date: Nov. 18, 2019

(87) PCT Pub. No.: WO2018/213839
PCT Pub. Date: Nov. 22, 2018

(65) Prior Publication Data
US 2020/0178938 A1    Jun. 11, 2020

Related U.S. Application Data

(60) Provisional application No. 62/541,942, filed on Aug. 7, 2017, provisional application No. 62/508,884, filed on May 19, 2017.

(51) Int. Cl.
*A61B 8/08* (2006.01)
*A61B 8/06* (2006.01)
(Continued)

(52) U.S. Cl.
CPC ............. *A61B 8/5223* (2013.01); *A61B 8/06* (2013.01); *A61B 8/0891* (2013.01); *A61B 8/14* (2013.01);
(Continued)

(58) Field of Classification Search
CPC .... G16H 50/30; A61B 8/5246; A61B 8/0891; A61B 8/5276; A61B 8/5223; A61B 8/06;
(Continued)

(56) References Cited

U.S. PATENT DOCUMENTS

| 6,217,520 B1 | 4/2001 | He |
| 2005/0090747 A1 | 4/2005 | Clark |

(Continued)

FOREIGN PATENT DOCUMENTS

WO    2020/077202 A1    4/2020

OTHER PUBLICATIONS

Int'l Search Report and Written Opinion from parent PCT/US2018/033723, dated Nov. 9, 2018, 18 pages.
(Continued)

*Primary Examiner* — Bo Joseph Peng
(74) *Attorney, Agent, or Firm* — Quarles & Brady LLP

(57) ABSTRACT

Methods and systems for producing a visually-perceived representation of a sub-millimeter-sized blood vessel located at a depth of many centimeters in the biological tissue, in which the background clutter is suppressed (by at least 30 dB using SVT and additional 23 dB using a combination of morphology filtering and vessel enhancement filtering) as compared to an image obtained with the use of a B-mode ultrasound imaging, while at the same time maintaining the morphology of the blood vessel.

15 Claims, 20 Drawing Sheets

(51) Int. Cl.
*A61B 8/14* (2006.01)
*A61B 8/00* (2006.01)

(52) U.S. Cl.
CPC ............ *A61B 8/463* (2013.01); *A61B 8/5246* (2013.01); *A61B 8/5276* (2013.01); *A61B 8/4444* (2013.01); *A61B 8/488* (2013.01)

(58) Field of Classification Search
CPC ......... A61B 8/463; A61B 8/14; A61B 8/4444; A61B 8/488
See application file for complete search history.

(56) References Cited

U.S. PATENT DOCUMENTS

| | | |
|---|---|---|
| 2005/0277835 A1 | 12/2005 | Angelsen et al. |
| 2008/0242994 A1 | 10/2008 | Tamura |
| 2014/0039320 A1 | 2/2014 | Jespersen et al. |

OTHER PUBLICATIONS

Demene, et al., Spatiotemporal Clutter Filtering of Ultrafast Ultrasound Data Highly Increases Doppler and Ultrasound Sensitivity, IEEE Transactions On Medical Imaging, IEEE Service Center, Piscataway, NJ, US, vol. 34. No. 11, Nov. 2, 2015; pp. 2271-2285.
Kruse, et al., A new high resolution color flow system using an eigendecomposition-based adaptive filter for clutter rejection, IEEE Transactions On Ultrasonics, Ferroelectrics and Frequency Control, IEEE, US, vol. 49, No. 10. Oct. 2, 2002 (Oct. 2, 2002), pp. 1384-1399.
Frangi, A.F. et al., 1998. "Multiscale vessel enhancement filtering," Medical Image Computing and Computer-Assisted Intervention—MICCAI'98 vol. 1496 of the series Lecture Notes in Computer Science pp. 130-137.
Gessner, R.C. et al., "Mapping Microvasculature with Acoustic Angiography Yields Quantifiable Differences between Healthy and Tumor-bearing Tissue Volumes in a Rodent Model," Radiology, vol. 264, pp. 733-740, 2012.
Lindsey, B.D. et al., "Acoustic characterization of contrast-to-tissue ratio and axial resolution for dual-frequency contrast-specific acoustic angiography imaging," IEEE Transactions on Ultrasonics, Ferroelectrics, and Frequency Control, vol. 61, pp. 1668-1687, 2014.
Najman L. et al., "Introduction to Mathematical Morphology," in Mathematical Morphology, ed: John Wiley & Sons, Inc., 2013, pp. 1-33.
Sato, Y. et al., "Three-dimensional multi-scale line filter for segmentation and visualization of curvilinear structures in medical images," Medical Image Analysis, vol. 2, pp. 143-168, 1998.
Song, P. et al., "Ultrasound Small Vessel Imaging with Block-Wise Adaptive Local Clutter Filtering," IEEE Transactions on Medical Imaging, vol. PP, pp. 1-1, 2016.
Van Den Boomgard, R, et al., "Methods for Fast Morphological Image Transforms Using Bitmapped Images," Computer Vision, Graphics, and Image Processing: Graphical Models and Image Processing, vol. 54, No. 3, pp. 252-254, May 1992.
Wang, G. et al., "Morphological Background Detection and Illumination Normalization of Text Image with Poor Lighting," PLOS ONE, vol. 9, p. e110991, 2014.
Yu A.C.H. et al., "Eigen-based clutter filter design for ultrasound color flow imaging: A review," IEEE Trans. Ultrason. Ferroelectr. Freq. Control, vol. 57, No. 5, pp. 1096-1111, May 2010.
Zagorchev, L. et al., "Micro computed tomography for vascular exploration," Journal of Angiogenesis Research, vol. 2, pp. 7-7, 2010.
Zhang, H. et al., "3D contrast-enhanced MR angiography," Journal of Magnetic Resonance Imaging, vol. 25, pp. 13-25, 2007.

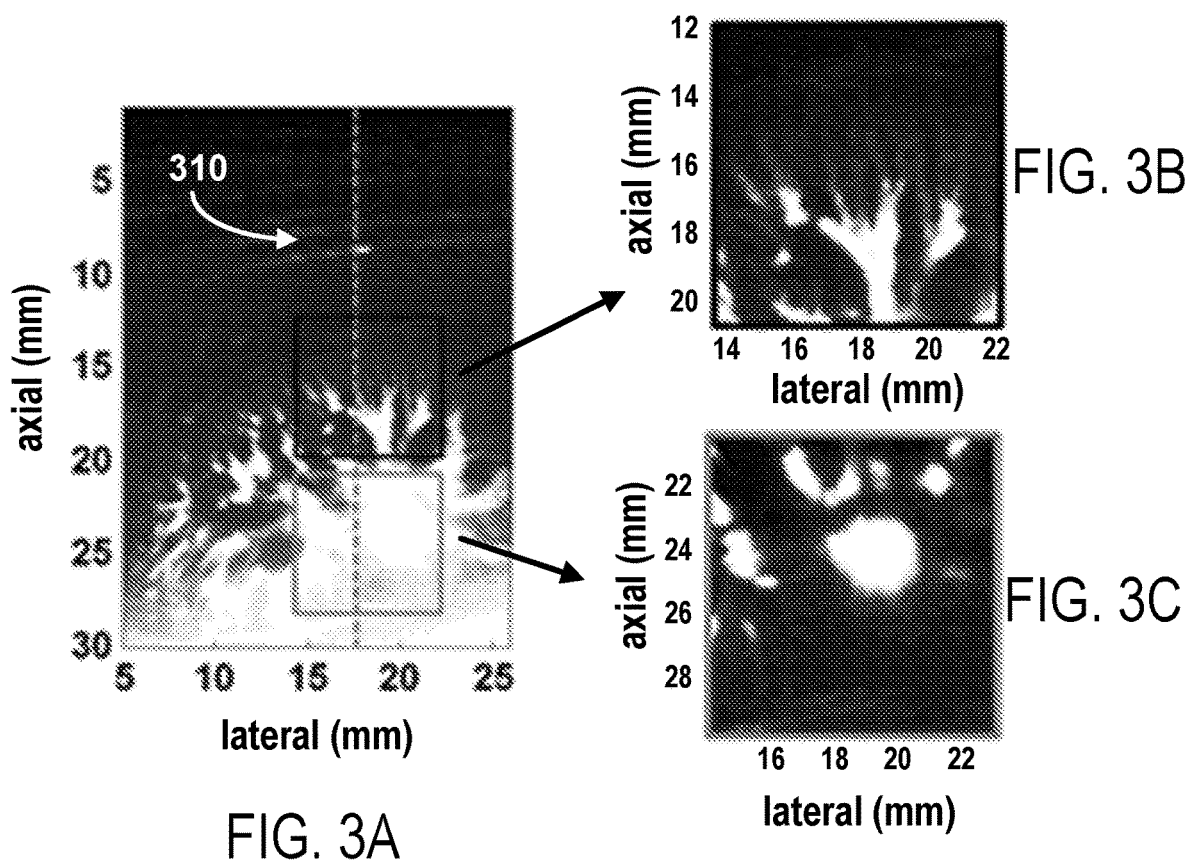
FIG. 3A
FIG. 3B
FIG. 3C
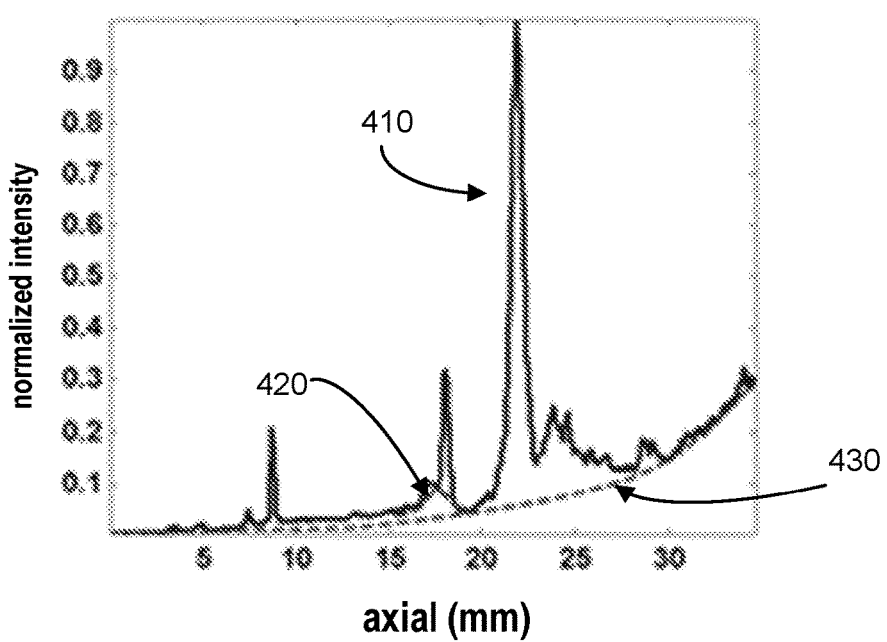
FIG. 4

| | Vessel 1 | | | Vessel 2 | | | Vessel 3 | | | Vessel 4 | | | All |
|---|---|---|---|---|---|---|---|---|---|---|---|---|---|
| | L-PSL | R-PSL | $\overline{PSL}$ | L-PSL | R-PSL | $\overline{PSL}$ | L-PSL | R-PSL | $\overline{PSL}$ | L-PSL | R-PSL | $\overline{PSL}$ | Min $\overline{PSL}$ |
| SVT | 54.99 | 60.7 | 57.68 | 24.44 | 31.26 | 27.85 | 42.81 | 39.93 | 41.37 | 14.65 | 12.12 | 13.39 | 13.39 |
| THF | ∞ | ∞ | ∞ | ∞ | ∞ | ∞ | ∞ | ∞ | ∞ | ∞ | 76.26 | ∞ | ∞ |
| VEF | ∞ | ∞ | ∞ | ∞ | ∞ | ∞ | ∞ | ∞ | ∞ | ∞ | ∞ | ∞ | ∞ |

FIG. 8E

|  | Vessel 1 ||| Vessel 2 ||| Vessel 3 ||| Vessel 4 |||
| --- | --- | --- | --- | --- | --- | --- | --- | --- | --- | --- | --- | --- |
|  | L-PSL | R-PSL | $\overline{PSL}$ | L-PSL | R-PSL | $\overline{PSL}$ | L-PSL | R-PSL | $\overline{PSL}$ | L-PSL | R-PSL | $\overline{PSL}$ |
| SVT | - | 14.17 | 14.17 | 9.38 | 8.22 | 8.80 | 3.17 | 4.85 | 4.01 | 5.38 | 5.87 | 5.62 |
| THF | - | 57.41 | 14.17 | 45.13 | 46.92 | 46.03 | 28.8 | ∞ | ∞ | ∞ | ∞ | ∞ |
| VEF | - | 114.94 | 68.89 | 106.49 | 47.35 | 76.92 | 23.52 | ∞ | ∞ | ∞ | ∞ | ∞ |

|  | Vessel 5 ||| Vessel 6 ||| Vessel 7 ||| All |
| --- | --- | --- | --- | --- | --- | --- | --- | --- | --- | --- |
|  | L-PSL | R-PSL | $\overline{PSL}$ | L-PSL | R-PSL | $\overline{PSL}$ | L-PSL | R-PSL | $\overline{PSL}$ | Min $\overline{PSL}$ |
| SVT | 6.72 | 4.35 | 5.54 | 7.23 | 9.48 | 8.36 | 5.99 | 3.33 | 4.66 | 4.01 |
| THF | ∞ | 29.64 | ∞ | 39.20 | 93.79 | 66.45 | 81.53 | 24.88 | 53.21 | 14.17 |
| VEF | ∞ | 42.59 | ∞ | 40.41 | 43.80 | 42.11 | 40.05 | 34.33 | 37.19 | 37.19 |

FIG. 9E

SYSTEM AND METHOD FOR VISUALIZATION OF TISSUE MICROVASCULAR USING ULTRASOUND

CROSS-REFERENCE TO RELATED APPLICATIONS

This application is a 371 U.S. National Phase Application of PCT/US2018/033723, filed May 21, 2018, which claims the benefit of U.S. Provisional Patent Application Ser. No. 62/508,884, filed on May 19, 2017, and entitled "SYSTEM AND METHOD FOR VISUALIZATION OF TISSUE MICROVASCULAR USING ULTRASOUND," and of U.S. Provisional Patent Application No. 62/541,942, filed on Aug. 7, 2017, and entitled "SYSTEM AND METHOD FOR VISUALIZATION OF TISSUE MICROVASCULATURE USING ULTRASOUND," all of which are herein incorporated by reference in their entirety.

STATEMENT REGARDING FEDERALLY SPONSORED RESEARCH

This invention was made with government support under CA195527, CA148994, and EB017213 awarded by the National Institutes of Health. The government has certain rights in the invention.

BACKGROUND

Imaging of the sub-millimeter size vasculature, seated many centimeters deep inside the body, still remains a challenging task in medical imaging. Conventionally, desired images are acquire with the use of contrast-enhanced magnetic resonance and microscopic computed tomography (micro-CT). The usefulness of these methods in research and clinical applications, however, are limited both operationally and cost-wise: to implement any of these, an injection of a contrast enhancement agent is required, and the costs are high, imaging times are long, and portability of these modalities is low. Doppler ultrasound approach has also been traditionally used for real-time imaging of the tissue blood vessels and large-scale hemodynamics. The use of this method, however, continues to suffer from low cluttered tissue areas (such as abdominal organs, for example) have to be imaged. Overall, maps of blood vessel(s) of the tissue obtained as a result of employing these imaging methods are highly fragmented, which makes the interpretation of the morphological features of vessel network extremely complicated if not impractical.

The recently-introduced ultrasensitive Doppler ultrasound-based modality for visualization of tissue vascularity with sub-millimeter sizes is based on plane-wave imaging with multiple-angle compounding, and enables high quality imaging within a wide field-of-view (FOV) at high frame rates, and analysis of the coherence in both spatial and temporal domains. Based on this principle and using singular value thresholding (SVT), high-quality visualization of the vasculature at micron levels has been recently reported, as described for instance in *IEEE Transactions on Medical Imaging*, vol. 34, pp. 2271-2285, 2015.

The main underlying assumption of this recently-introduced methodology is that motion of the bulk of the tissue and blood flow leave different signatures in the ultrasound backscattered echoes, which occupy two different sub-spaces: while tissue clutter signal mostly lies in a highly correlated sub-space that constitutes more than 99% of the backscattered energy, blood flow presents in a weakly correlated sub-space with extremely week amplitudes (at levels of more than 30 dB below the clutter signal, for example). With this assumption, the SVT of a temporal covariance matrix can facilitate the separation of the two sub-spaces via a thresholding operation based on signal coherence.

What the above assumption that underlies the SVT method(s) does account for, however, is that—in addition to blood signal—auxiliary noise is also present in the weakly correlated sub-space. Such additive noise is caused by electronic devices as well as random rearrangements of the ultrasound diffuse scattering patterns, known as speckles. Ultrasound images are known be strongly susceptible to (and, as a result, the imaging process suffering from) intensity variations caused by multiple physical phenomena such as specular reflections, edge artifacts, shadowing due to partial or global tissue absorption of ultrasonic energy, to name just a few. These variations in signal amplitude cannot be directly embedded in to equalize the subspace amplitudes resulted from the SVT. Hence, vessel structures derived from SVT are visualized and visible at different dynamic ranges at different depths (that is, a dynamic range of the appropriate signal is changed as the imaging depth increases, for example) and locations.

With the above analysis, a person of skill in the art will readily appreciate that the currently used SVT-based method performs well only for superficial and mostly homogeneous tissue vasculature imaging (where uncorrelated additive noise contribution is not significant, as compared to the total ultrasound backscattered echo). In more realistic situations, however, maintaining the dynamic range constant may cause low visibility of the vessels in some part of the image or a saturated image of the vessels in other parts. Related art attempted to alleviate this problem by shrinking the spatial domain for SVD decomposition such that a constant signal power can be assumed throughout the domain. However, in addition to excessive computational cost, the main drawback of such method is the reduction of number of basis vectors for decomposition of the tissue and blood signal components. This reduced space, in turn, can limit the spatial resolution of the final images as subtle blood dynamics in small vessels may not be well represented in the reduced signal space. Problems left to be resolved by the SVT-based methodologies remain to be addressed.

SUMMARY OF THE DISCLOSURE

The present disclosure addresses the aforementioned drawbacks by providing a method for generating an image depicting tissue microvasculature using an ultrasound system. The method includes, with an ultrasound imaging system, recording a sequence of first images of a blood vessel of a tissue, said blood vessel having a first spatial scale. The sequence of first images is transformed into a second image by separating a weakly-correlated ultrasound data of the sequence of first images from a highly-correlated ultrasound data of the sequence of first images, wherein said separating is carried out based on a pre-determined threshold value, wherein said weakly-correlated ultrasound data represents blood activity, and wherein said highly-correlated ultrasound data represents more than 99% of energy in singular values. A third image is generated by reducing a spatially-variant background signal corresponding to features having a second spatial scale from the second image using a circular morphology structure by at least 10 dB. The third image is transformed into a fourth image by equalizing variations of intensity across the third image to compensate for ultrasound fluctuations caused by relative orientation of a probe of the ultrasound imaging system and the blood vessel. The visibility of said blood vessel presented is adjusted for viewing while forming a visually-perceived output, from said ultrasound imaging system, in which the third image has been modified based on representation of said blood vessel as a tubular structure.

It is another aspect of the present disclosure to provide a method for generating an image depicting tissue microvasculature using an ultrasound system. The method includes acquiring ultrasound echo data from a region-of-interest in a subject with an ultrasound system, wherein the region-of-interest contains tissue microvasculature. Clutter removed data are generated by performing a clutter removal algorithm on the ultrasound echo data, wherein the clutter removal algorithm is implemented with a hardware processor and a memory. Spectrum data are generated by performing a temporal Fourier transform on the clutter removed data. Negative frequency data in the spectrum data are stored as negative frequency spectrum data, and positive frequency data in the spectrum data are stored as positive frequency spectrum data. A first image is reconstructed from the negative frequency spectrum data, and a second image is reconstructed from the positive frequency spectrum data. A third image that depicts tissue microvasculature is generated by combining the first image and the second image in order to reduce artifacts and noise.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 3A: an SVT filtered image of kidney vasculature in a healthy volunteer; FIGS. 3B, 3C: selected small area images from small rectangular boxes shown in FIG. 3A are presented at dynamic ranges tuned to each region signal intensity.

FIG. 4: local and global signal intensity variations overlaid on a line segment from the gross image.

FIG. 8E: Table 1 with summary of itemized parameters.

FIG. 9E: Table 2 with summary of itemized parameters.

DETAILED DESCRIPTION

Figure 1:
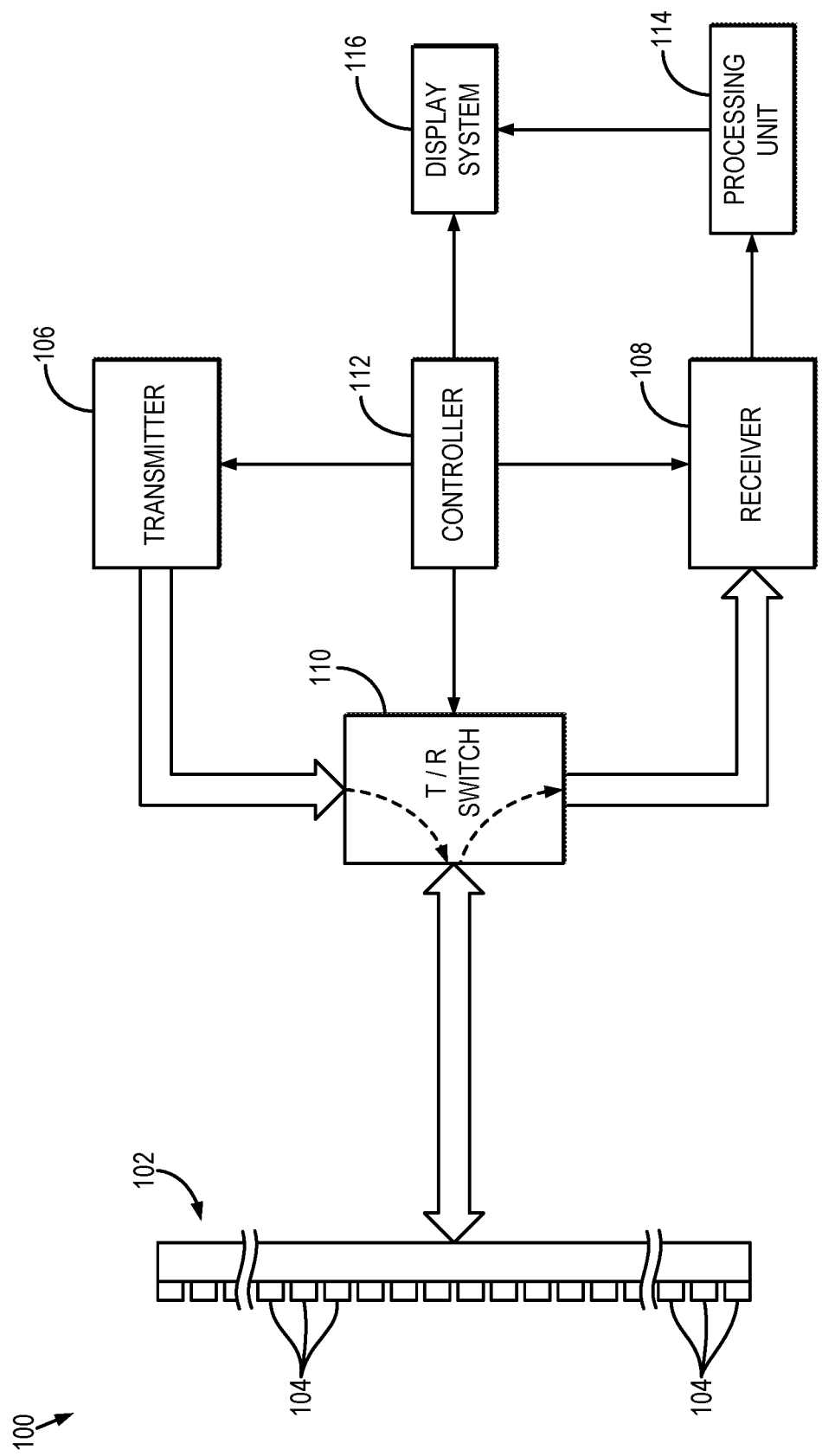
FIG. 1 provides an example of an ultrasound system that can be used to implement an embodiment of the invention.

Described here are systems and methods for enhancing ultrasonic visualization of tissue microvasculature in a manner that improves image segmentation and estimation of blood flow speed(s) in tissue small vessel network.

Embodiments of the present disclosure are directed to enhancement of visualization of the small vessels in both power Doppler mode and color flow imaging (of the tissue), which images have been obtained with the use of singular value thresholding (SVT) "clutter removal" approach of related art. Some other embodiments of the present disclosure are directed to enhancing the visualization of small vessels through artifact and noise suppression. Still other embodiments of the present disclosure are directed to enhancing the visualization of small vessels through motion compensation.

Previously, the SVT was shown to be a powerful tool in separating highly correlated tissue clutter backscatter signals from the blood signal, allowing the small vessels to be visualized at high resolutions that could not be achieved using conventional Doppler imaging methods. However, a number of undesired features in SVT-derived images continued to prevent further image-based assessment of the tissue structure, such as analysis of the vessel morphology, for example. Time-gain compensation (TGC) is sometimes used to visualize different depths of tissue within the ultrasound field of view using at a given dynamic range when using regular B-mode imaging. If TGC is employed. The most dominant remaining after the SVT processing is a depth-dependent background signal, which progressively increases with depth. This persistent problem mainly stems from the fact that conventional singular value decomposition methods give or assign equal weights to all contributing vectors regardless of the depth. It was determined that, as a result of such assignment, even after the exclusion of the clutter subspace the synthesized images contained a background signal with varying amplitude. An additional problem with SVT-images is related to severe local intensity changes in ultrasound echo signal, which may result from strongly-reflecting tissue elements and/or spatial orientation(s) of the tissue inhomogeneity. Such local intensity changes may, in turn, cause local variations in the background signal present in the SVT derived vessel images.

The above-identified effects aggregately limit the visibility of the vessels in images at different size scales and depths, and effectively prevent the use of segmentation algorithms (which require complete separation of the target vessel areas from the background). The strength and advantage of the proposed methodology is that it solves these problems with the use of a two-step approach, utilizing a morphology-based filtering (configured to remove background signals that appear at size scales larger than a specified, predetermined scale or range) in the form of top-hat filtering (THF) with a circular structuring element. The diameter of this structuring element was judiciously defined to be larger than the largest desired vessel size, and is a parameter of choice to be adjusted. For example, when the microvasculature in a thyroid nodule next to the main carotid artery is to be imaged (and while both the microvasculature and the artery represent vessels), the structuring element size is chosen to be small enough to remove the artery but large enough to preserve larger vessels of interest in the thyroid gland and inside potential thyroid nodule. Additionally, THF is a general term for a group of background removal algorithms based on opening morphology operations. Other methods can replace THF but will result in loss of resolution or significantly increase computational cost.

As a result of such combination, most of the background blanket signals are removed from the imaging data, and local intensity variations are compensated such that better connectivity can be observed in vessel maps throughout the entire imaging domain. The proposed algorithm then progresses with a Hessian-based vessel enhancement filtering to further improve the background suppression and vessel visibility. In addition to visible enhancement provided by the VEF, significant quantitative gains were achieved after each processing stage as summarized in Table 1 (FIG. 8E) and Table 2 (FIG. 9E). THF alone provides at least 10 dB as compared to SVT and THF+VEF, provided a minimum gain of about 23 dB in separation of vessels from the background minimal impact on spatial resolution. The combined gain of (SVT+THF+VEF) is at least 53 dB, as compared to normal B-mode imaging.

The disclosed method is the first attempt, to the best of the knowledge of the inventors, to apply vessel filtering to ultrasonically detected microvasculature: there appear to be no data available in the literature to compare with the discussed-below results, at least in terms of achieved gain. The 23 dB gain reported here is the minimum achievable gain, while the gain figures can be extremely high because the combination of (THF+VEF) processes can potentially substantially completely remove the background from an image, thereby resulting in substantially infinite contrast to noise ratio.

The efficient background suppression achieved by the proposed method enables efficient segmentation and analysis of the morphological features of the vascular structures. Perfusion is considered as a hallmark for malignancy as blood supply is provided by a process called angiogenesis. While related art (in particular, R. C. Gessner et al., "Mapping Microvasculature with Acoustic Angiography Yields Quantifiable Differences between Healthy and Tumor-bearing Tissue Volumes in a Rodent Model," *Radiology*, 2012; 264:733-740) had to utilize contrast-enhanced acoustic angiography to demonstrate that the morphological features can serve as potential biomarkers for identification of cancerous tumors, the present methodology results in so significant processing gains that obtaining continuous vessel maps simply do not require injection of contrast agents in the imaged tissue, allowing to achieve the sought-after imaging of microvasculature of the tissue substantially without side-effect and patient discomfort that are conventionally associated with the administration of a contrast agent. Further, the proposed methodology ensures that high-quality imaging is successfully carried out at larger depths into the tissue as compared to acoustic angiography, at least because the vessel images are derived with the use of the fundamental frequencies instead of higher harmonics as in related art.

FIG. 1 illustrates an example of an ultrasound system 100 that can implement the methods described in the present disclosure. The ultrasound system 100 includes a transducer array 102 that includes a plurality of separately driven transducer elements 104. The transducer array 102 can include any suitable ultrasound transducer array, including linear arrays, curved arrays, phased arrays, and so on. Similarly, the transducer array 102 can include a 1D transducer, a 1.5D transducer, a 1.75D transducer, a 2D transducer, a 3D transducer, and so on.

When energized by a transmitter 106, a given transducer element 104 produces a burst of ultrasonic energy. The ultrasonic energy reflected back to the transducer array 102 (e.g., an echo) from the object or subject under study is converted to an electrical signal (e.g., an echo signal) by each transducer element 104 and can be applied separately to a receiver 108 through a set of switches 110. The transmitter 106, receiver 108, and switches 110 are operated under the control of a controller 112, which may include one or more processors. As one example, the controller 112 can include a computer system.

The transmitter 106 can be programmed to transmit unfocused or focused ultrasound waves. In some configurations, the transmitter 106 can also be programmed to transmit diverged waves, spherical waves, cylindrical waves, plane waves, or combinations thereof. Furthermore, the transmitter 106 can be programmed to transmit spatially or temporally encoded pulses.

The receiver 108 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 106 and the receiver 108 can be programmed to implement a high frame rate. For instance, a frame rate associated with an acquisition pulse repetition frequency ("PRF") of at least 100 Hz can be implemented. In some configurations, the ultrasound system 100 can sample and store at least one hundred ensembles of echo signals in the temporal direction.

The controller 112 can be programmed to implement an imaging sequence using the techniques described in the present disclosure, or as otherwise known in the art. In some embodiments, the controller 112 receives user inputs defining various factors used in the design of the imaging sequence.

A scan can be performed by setting the switches 110 to their transmit position, thereby directing the transmitter 106 to be turned on momentarily to energize transducer elements 104 during a single transmission event according to the selected imaging sequence. The switches 110 can then be set to their receive position and the subsequent echo signals produced by the transducer elements 104 in response to one or more detected echoes are measured and applied to the receiver 108. The separate echo signals from the transducer elements 104 can be combined in the receiver 108 to produce a single echo signal.

The echo signals are communicated to a processing unit 114, which may be implemented by a hardware processor and memory, to process echo signals or images generated from echo signals. As an example, the processing unit 114 can produce images of small vessels using the methods described in the present disclosure. Images produced from the echo signals by the processing unit 114 can be displayed on a display system 116.

The memory may be random access memory (RAM), read-only memory (ROM), flash memory or any other memory, or combination thereof, suitable for storing control software or other instructions and data. Those skilled in the art should would readily appreciate that instructions or programs defining the operation in accordance with embodiments described in the present disclosure may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the methods described in the present disclosure may be embodied in software, the functions to implement those methods may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

The systems and methods described in the present disclosure stem from the realization that purification, cleaning, or enhancement of a gross SVT-based image of the tissue vasculature can be achieved by combining a multiscale vessel analysis with a morphology filtering method that retains information about small vessel structures while the local and global imaging background is removed. In some embodiments, the SVT-based images should preferably exhibit vessel structures at dynamic ranges that are not constant, but differ with depth at which such structures are located, and should also possess variations caused at least by changing orientation of vessel(s) and direction of blood flow. In particular, the modification of the morphology filtering method includes tuning its critical parameters to account for size(s) of the vessel structures in question.

Image Acquisition and Clutter Removal with the Use of Global SVT

Figure 2A:
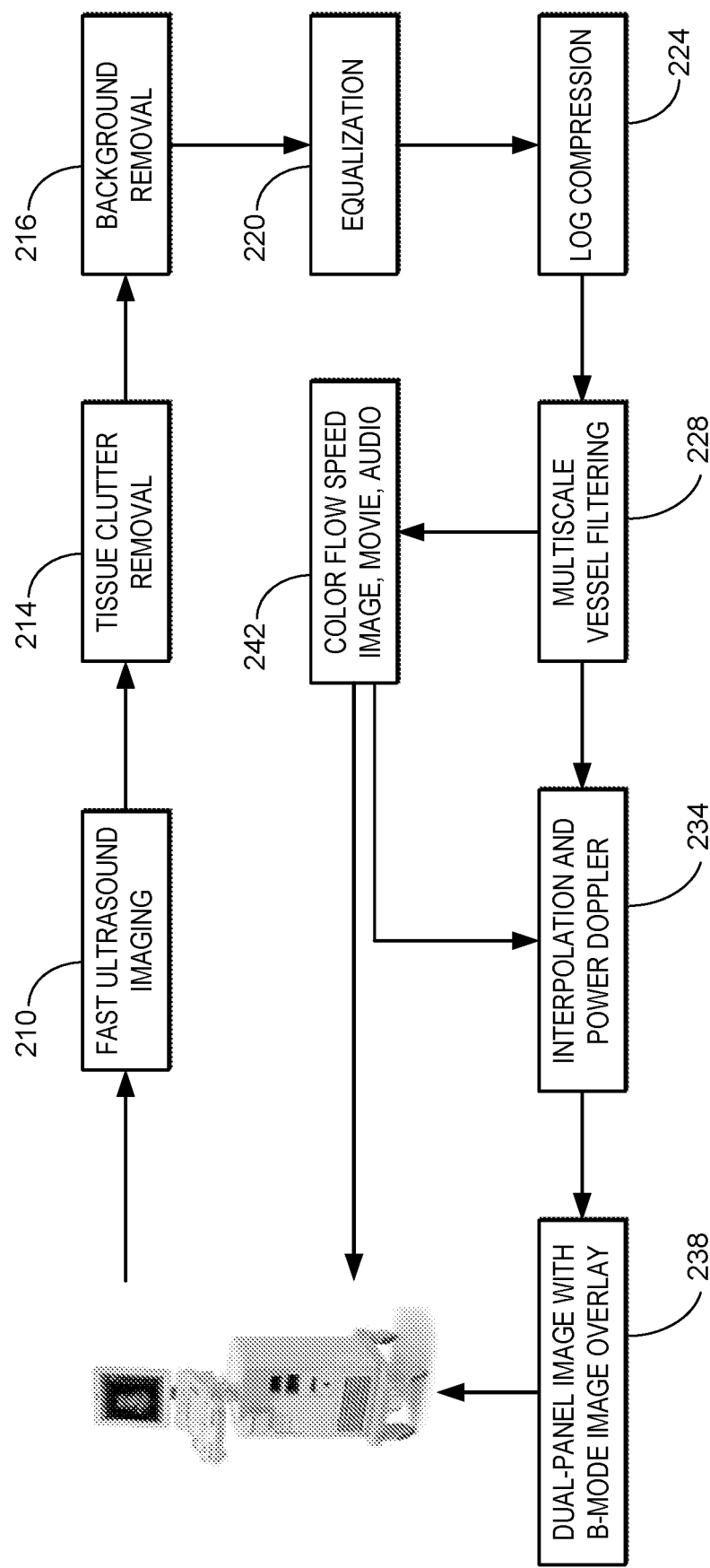
FIG. 2A presents a generalize flow chart of the process according to an embodiment of the invention.

The generalized flow-chart of an embodiment of the process of the invention—which is discussed in detail below—is presented in FIG. 2A. Each of the constituent processing steps 210, 214, 216, 220, 224, 228, 234, 238, 242 is addressed in more detail below.

Figures 2B, 2C:
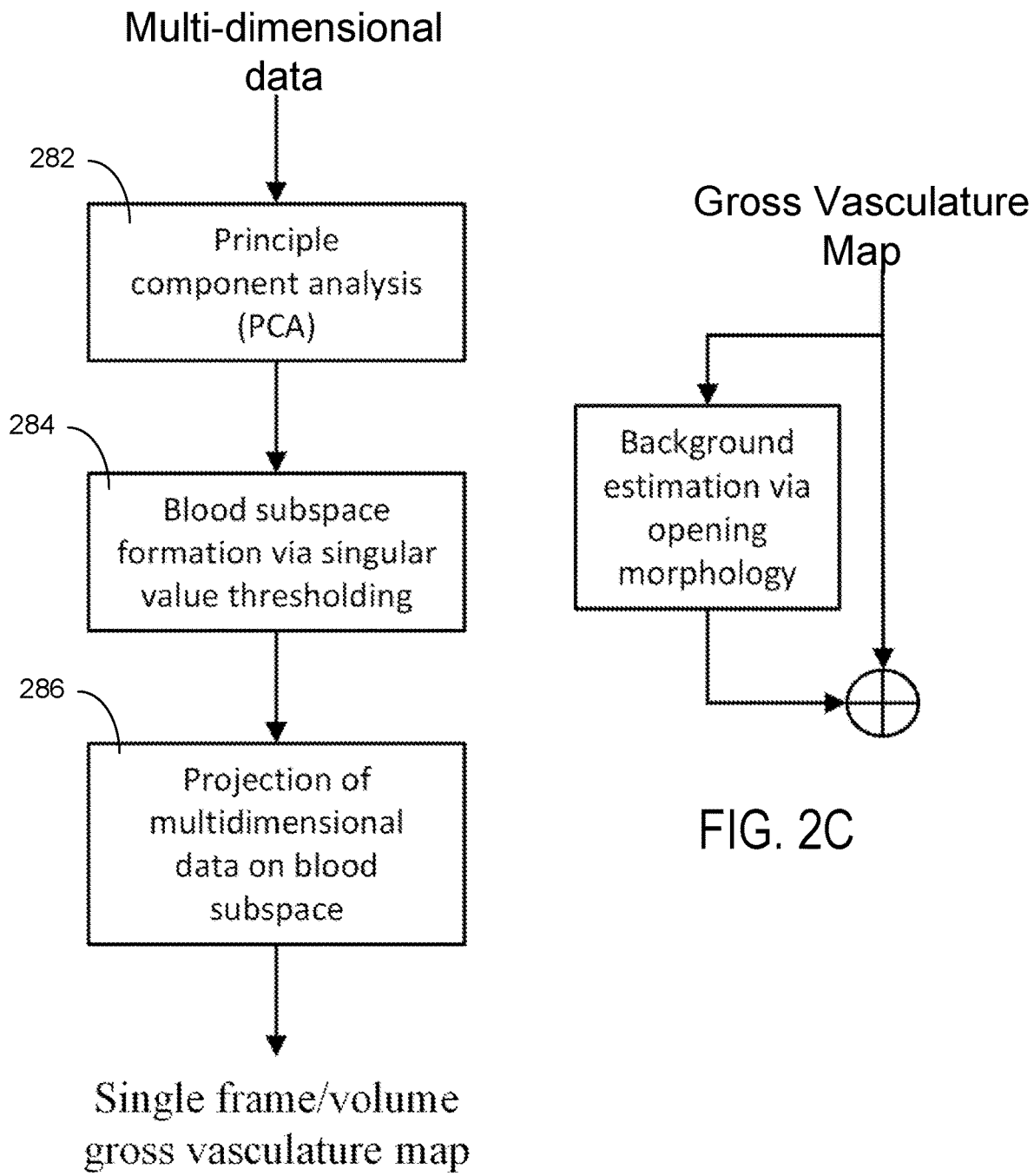
FIG. 2B presents a block scheme illustrating general flow of the process of tissue clutter removal according to an embodiment of the invention.
FIG. 2C illustrates a block diagram of the process of background clutter removal from an image of vasculature.

Generally, and in reference to a schematic diagram of FIG. 2B, at the first stage of the image-transformation process and after the raw ultrasound data have been acquired with the use of, for example, fast plane wave ultrasound imaging with coherent compounding at hundreds to thousands frames per second (or, alternatively, with beam-formed line-by-line scanning in a limited field; or a set-up illustrated in FIG. 1), the entire spatial-temporal data for building the orthogonal basis (see 282) is incorporated and SVT is used at 284 to remove the clutter signal from the entire domain of data. Alternatively or additionally, tissue clutter removal may involve blood sub-space projection, 286. The thresholding procedure provides a subspace that represents the blood activity and uncorrelated background noise. The original multi-dimensional data may be projected into this sub-space to form a single frame (in case of planar imaging) or a single volume (in case of volume imaging).

Generally, the present visualization approach preferably utilizes fast ultrasound imaging. (For example, fast plane wave ultrasound imaging with coherent compounding may be used to acquire raw ultrasound data at hundreds to thousands frames per second. Alternatively, beam-formed line-by-line scanning in a limited field may be used.) Tissue clutter may then be removed from the raw ultrasound data. This can involve a multi-dimensional signal decomposition. Methods for separating tissue ultrasound echo from blood ultrasound echo may include, for example, singular value thresholding, multi-resolution processing algorithms (such as wavelet and wave packet), and blind source separation algorithms such as independent component analysis. Tissue displacement and blood activity present distinct spatiotemporal features in the ultrasound backscattered data. Traditionally, high pass or band pass filtering has been used to reduce tissue clutter from blood activity data. With the emergence of fast ultrasound using plane wave imaging with multiple angle compounding, large data ensembles can be acquired from a large spatial field of view at very high frame rates. This enables statistical analysis of the tissue and blood activity in a multidimensional domain. The tissue clutter removal may be based on eigenanalysis of a covariance matrix. Tissue clutter may be removed based on thresholding of highly correlated data with significant singular values while blood activity is separated as a weakly correlated subspace. Alternatively or additionally, tissue clutter removal may involve blood sub-space projection. The thresholding procedure provides a subspace that represents the blood activity and uncorrelated background noise. The original multi-dimensional data may be projected into this sub-space to form a single frame (in case of planar imaging) or a single volume (in case of volume imaging). Background removal may utilize methods of removing a spatially-variant background signal from a clutter-free gross vessel image. Examples of such methods include morphology filtering such as top-hat filtering, moving average filtering, Savitzky-Golay filtering, and non-local mean background removal. Background estimation may be based on an "opening morphology" technique. For example, after removing the tissue clutter, the resulting data represents a weakly correlated subspace that contains mostly blood activity. However, this data also includes additive white noise (statistically uncorrelated) that progressively increases with depth due to ultrasound signal attenuation. In this step, a morphological structuring kernel may be used to extract the randomly distributed background from the vessel map.

Below, the details of the clutter-removal procedure are discussed. See FIG. 2B.

For a data point at depth z, the ultrasound raw data can be represented as, $$r(z,t)=e^{-\alpha z}s_c(z,t0+e^{-\alpha z}s_b(z,t)+n(t) \quad (1);$$

where $s_c$ and $s_b$ are the clutter and tissue components respectively, n is the additive white Gaussian noise due to electrical components and $\alpha$ is the tissue attenuation rate with depth which is assumed to be constant. Let's assume we arrange a stack of this data in a matrix in the form of, $$R\begin{bmatrix} r_{11} & \cdots & r_{1N} \\ \vdots & \ddots & \vdots \\ r_{M1} & \cdots & r_{MN} \end{bmatrix} = \sum_{i=1}^{min\{M,N\}} \lambda_i u_i v_i^H; \quad (2)$$

where $r_{ij}$ represents the ultrasound raw data sampled at depth $z_i$ and time $t_j$. The right hand side of Eqn. (2) represents the SVD decomposition of matrix R, where eigenvalues are sorted as $\lambda_1 > \lambda_2 > \ldots > \lambda_{min\{M,N\}}$ and $u_i$ and $v_i$ are the $i^{th}$ eigenvector along the column and row spaces respectively. Matrix R is assumed to have full rank. An SVT algorithm can then be used to exclude the tissue clutter components which correspond to the largest singular values. Hence, the data matrix R spans two orthogonal sub-spaces: $S_c$=span$\{\lambda_1,\lambda_2,\ldots,\lambda_K\}$ that constitutes mostly the clutter signal and $S_{b+n}$=span$\{\lambda_{K+1},\lambda_2,\ldots,\lambda_{min\{M,N\}}\}$ that contains mostly blood signal and additive white noise. Hence the ultrasound data in Eqn. (1) can be presented as, $$r(z,t) = \underbrace{e^{-\alpha z}s_c(z,t)}_{\in s_c} + \underbrace{e^{-\alpha z}s_b(z,t) + n(t)}_{\in s_{b+n}}. \quad (3)$$

Since the thresholding is applied globally (with assigning equal weights to all signals through the depth of the tissue), the clutter contribution decreases with depth. Hence, in the clutter-free reconstructed image, as depth increases, blood and noise contributions become larger as compared to the clutter part. This can be clearly seen in FIG. 3A, presenting an SVT-based vessel image in a native kidney. In the presented dynamic range, the small cortical vessels can be easily recognized, while deeper parts of the image show saturation of image intensity and are, therefore, of insufficient quality. FIGS. 3B and 3C present two different regions of the image of FIG. 3A located at different depths and possessing two different dynamic ranges that are chosen/tuned for best visualization of each of these "sub" images. FIG. 4 shows the intensity variations along an axial line segment (dashed line 310 in FIG. 3A). As it can be seen, as depth increases, the vessel signature appears to be shifted (increased) by an additive background signal. This gradually increasing background signal is represented by a dashed line 430 in FIG. 4.

In addition to this global effect, local intensity changes can create small scale local variations or perturbations in the SVT reconstructed vessel image. An example is shown in FIG. 4, where a dashed line 420 is used to approximate these variations in the vicinity of vascular structure.

Therefore, a person of skill in the art will readily appreciate that this stage of the process produces a gross image of the tissue vasculature containing information about vessel structures at dynamic ranges that differ with depth of the vessel, preventing the clear display of all portions of the image and, therefore, reliable analysis of the image.

In order to remove these local and global variations, an embodiment of the invention utilizes a morphology filtering method (specifically, what's known as top-hat filtering) but—in contradistinction with related art—with parameters that are specifically tuned to the desired size of vessel structures that are being imaged.

Background Removal with the Use of Specifically-Modified Morphology Filtering

According to the idea of the invention, morphology filtering is applied for feature extraction from digital images where a structuring element is used in combination of a series of morphology operations. A top-hat filtering (THF) approach includes a background estimation, followed by a subtraction operation. For an image, x, the white top-hat filtering is defined as, $$x_w = x - x \circ SE \quad (4);$$

where SE is a morphology structuring element, and "∘" is an opening operation. The opening of set A by a structuring element B is defined, according to the "opening morphology" technique, as, $$A \circ B = (A \ominus B) \oplus B \quad \#;$$

where $\ominus$ and $\oplus$ are the erosion and dilation operations, respectively. Dilation and erosion are two of the basic mathematical morphology operations, and can be defined as, $$\begin{cases} A \oplus B = \bigcup_{b \in B} A_b & \text{Dilation} \\ A \ominus B = \bigcup_{b \in B} A_{-b} & \text{Erosion} \end{cases} \quad (5);$$

where $A_b$ and $A_{-b}$ is the translation of A by b and -b, respectively, and -b represents the binary negation.

Therefore, the white top-hat filtering of image x by structuring element SE results in, $$x_w = x - (x \ominus SE) \oplus SE \quad (6).$$

Figure 5A:
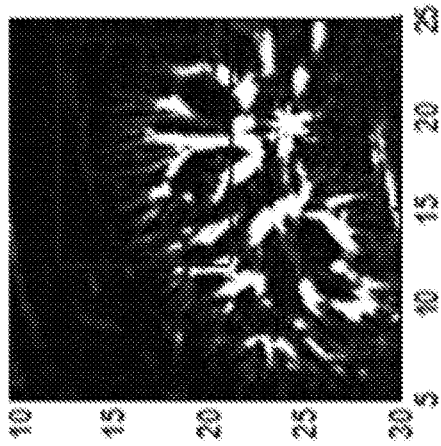
FIG. 5A: an SVT filtered image of kidney vasculature in a healthy volunteer.
Figure 5B:
FIG. 5B: background estimated using a circular structuring element.
Figure 5C:
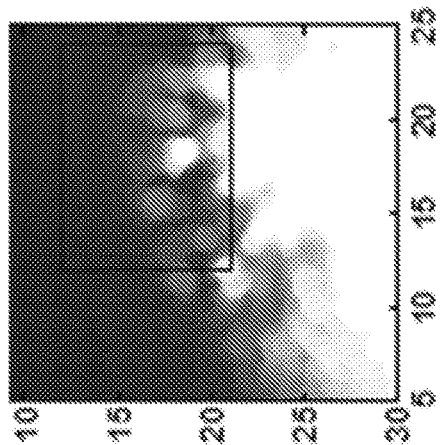
FIG. 5C: a top-hat filter image.
Figure 5D:
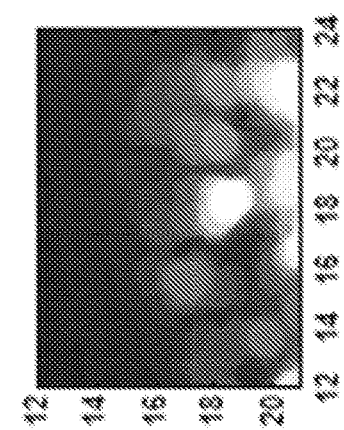
FIGS. 5D, 5E, and 5F present, on an enlarged scale, portions of images of FIGS. 5A, 5B, and 5C, respectively, outlined in such images with a rectangular box.
Figure 5E:
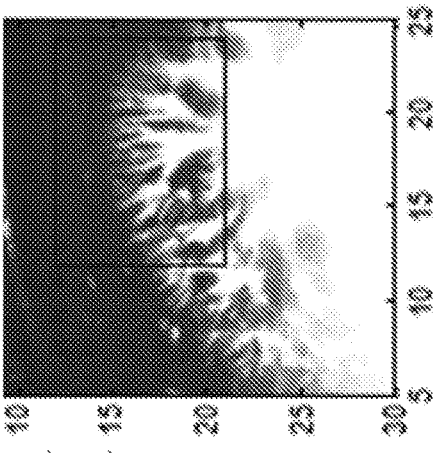
Figure 5F:

FIGS. 5A, 5B, 5C, 5D, 5E, and 5F depict the results of operation of the top-hat filtering algorithm on the kidney vessel image of FIG. 3A. Here, all images are shown using the same dynamic range. The structuring element used in this image transformation was a circle with a radius of 578 µm. FIG. 5B shows the estimated background, while FIG. 5C presents the vessel image after background removal. A person of skill will readily appreciate that the use of the top-hat filtering significantly removed most of the global and local background signal (compare with FIG. 1A) such that the entire vessel network being imaged can now be visualized using a single, constant for the same portion of the tissue regardless of the depth of the particular vessel, dynamic range. The subtracted image in FIG. 5B mainly contains a background signal that increases with depth. Additionally, it represents local variations due to local fluctuations of the background signal. Each of FIGS. 5D, 5E, and 5F depicts a smaller area or portion of the corresponding image of FIGS. 5A, 5B, 5C (see rectangular box in the corresponding images) for the gross image, background signal and top-hat filtered images, respectively. As can be easily visualized, the use of THF that has been modified according to the idea of the invention resulted in effective removal of the background signal with minimal impact on the quality of image(s) of small vessel structures.

Additional Image Enhancement Filtering

Despite the fact that modification of the morphology filtering according to the idea of the invention successfully produces greatly enhanced visibility of the vessel structures, the resulting images still may fall short of enabling quantitative analysis of the structural features of blood vessel network images. Even though the modified-THF-based images are free of background, slight intensity fluctuations may still affect the continuity of the images of vessels if a global thresholding is directly applied. Hence a vessel enhancement filtering is additionally used, as discussed below, to further improve the visibility and connectivity of the vascular structures and complete removal of the background via a thresholding mechanism.

The field of vessel filtering is not particularly new, due to a diverse range of angiography techniques developed over the past few years in different imaging modalities. One used technique is based on the analysis of tubular structures in a scale space domain with the use of eigenvalue value decomposition of the intensity Hessian matrix. The aim of these algorithms is to identify and enhance vessel-like structures while penalizing other unwanted components in the image.

Hessian-Based Multi-Vessel Enhancement Filtering (VEF)

In order to derive the formulation of a Hessian-based vessel filter, the notion of scale space derivative is introduced. The signal intensity, I, at a distance Sr from a pixel located at r can be written as, $$I(r+\delta r, s) \approx I(r,s) + \delta r^T \nabla_s + \delta r^T H_s \delta r \quad (7);$$

where $\nabla_s$ and $H_s$ are the Gaussian gradient vector and Hessian matrix at scale s, respectively. In scale space theory, true derivatives are replaced by bandlimited differentiation using a Gaussian kernel as, $$\frac{\partial}{\partial r} I(r, s) = s^\gamma I(r, s) * \frac{\partial}{\partial r} \Gamma(r, s); \quad (8)$$

where γ is a normalization parameter and Γ(r, s) is a Gaussian kernel defined as, $$\Gamma(r, s) = \frac{1}{2\pi s^2} e^{-\frac{\|r\|^2}{2s^2}}. \quad (9)$$

Based on this definition of differentiation, the Hessian matrix is calculated and eigenvectors and eigenvalues are derived. In 2-D domain, two eigenvalues, $\lambda_1$ and $\lambda_2$, are derived such that $|\lambda_2|>|\lambda_1|$. Based on this decomposition, the following scenarios may occur which are indicative of different patterns:
  A) Both are large positive numbers→blob-like pattern (dark intensity)
  B) Both are small negative numbers→blob-like pattern (bright intensity)
  C) $|\lambda_1|$ is a very small number, but $\lambda_2$ is a large positive number→tubular structure (dark intensity)
  D) $|\lambda_1|$ is a very small number but $\lambda_2$ is a small negative number→tubular structure (bright intensity)

Related art proposed a vessel enhancement and thresholding function as follows, $$\Delta_s \begin{cases} 0 & \lambda_2 > 0 \\ e^{-\frac{M^2}{2\beta^2}}\left(1 - e^{-\frac{\Lambda^2}{2\alpha^2}}\right) & \text{elsewhere} \end{cases}. \quad (10)$$

In Eqn. (10), $$M = \frac{\lambda_1}{\lambda_2}; \quad (11)$$

defines the eccentricity of second order ellipse and, $$\Lambda = \sqrt{\lambda_1^2 + \lambda_2^2} \quad (12);$$

is used to penalize any unstructured patterns, such as background noise, for example. Additionally, α defines the roll-off rate for soft-thresholding of the unstructured patterns and β is used to control the dynamic range of the output intensity.

An important aspect of using the scale space analysis stems from the fact the structures can be analyzed at different size scales simultaneously. In other words, the output of the vessel function, ΔS, is only sensitive to the shape similarities and not image intensities. Hence the final vessel image, Δ, can be formed by finding the maximum value of $\Delta_s$ over all estimated range of s, as, $$\Delta = \max_s \Delta_s. \quad (13)$$

Multi-Scale VEF: Analysis of an In Vivo Example

Figure 6C:
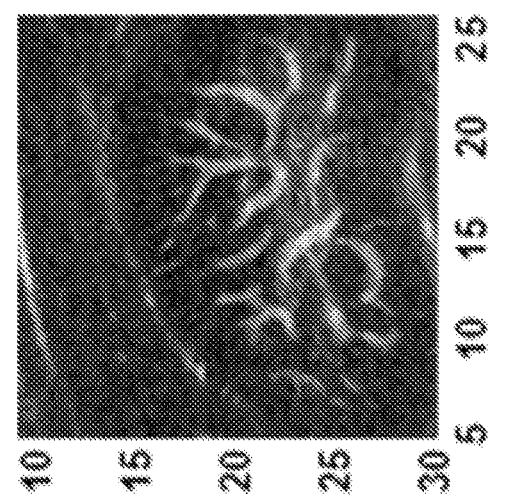
FIG. 6C: the vasculature image of FIG. 6B overlaid on the registered B-mode image of FIG. 6A.
Figure 6B:
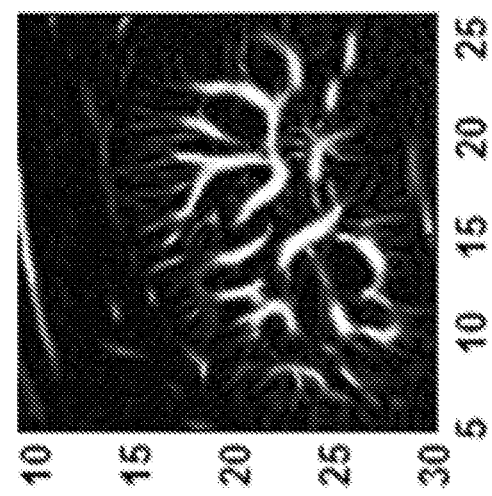
FIG. 6B: a vasculature image formed using 5-scale VEF method.
Figure 6A:
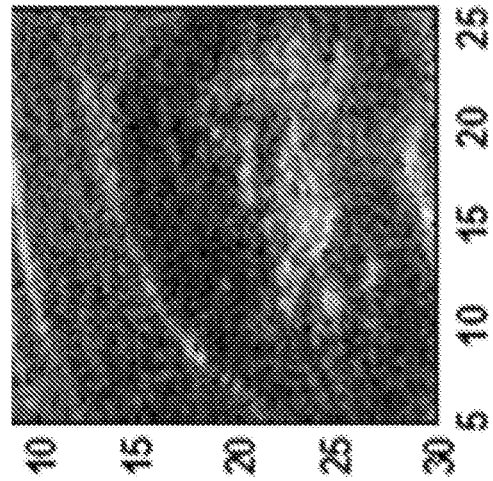
FIG. 6A: a B-mode image of the native kidney.

Image data obtained from the kidney vasculature, discussed above, were further processed with the multi-scale VEF method. For this purpose, a 5-scale VEF with vessel sizes of 116 µm, 231 µm, 347 µm, 462 µm and 578 µm was used. The vessel scale was chosen based on the smallest visible vessel size in the raw SVT-processed image. The largest scale was set equal to size of the structuring element used for top-hat filtering. The log-compressed top-hat filtered image was analyzed at different scales and the final image was formed based on Eqn. (13). Parameters α and β were empirically set to 0.6 and 50, respectively. FIG. 6A illustrates the B-mode image of the domain for vascular image reconstruction. FIG. 6B shows the final vasculature image after VEF, while overlap of the image of FIG. 6B on the corresponding B-mode image is shown in FIG. 6C. A skilled artisan will readily appreciate that the final image (FIG. 6C) provides a clear visualization of the nephritic vasculature for different sizes and dimensions of such vasculature. The image of FIG. 6C shows superior clarity almost independently from the depth and size of the vessels.

Figure 7A:
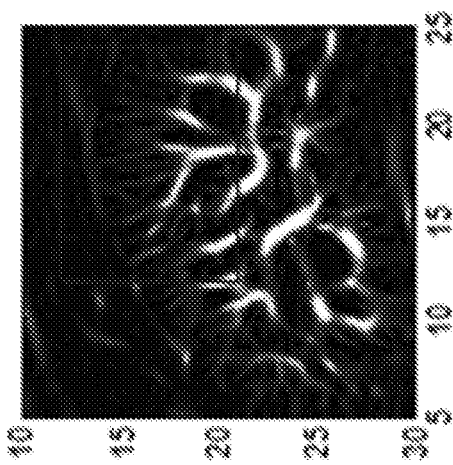
FIG. 7A: a gross vessel image after singular value decomposition.
Figure 7B:
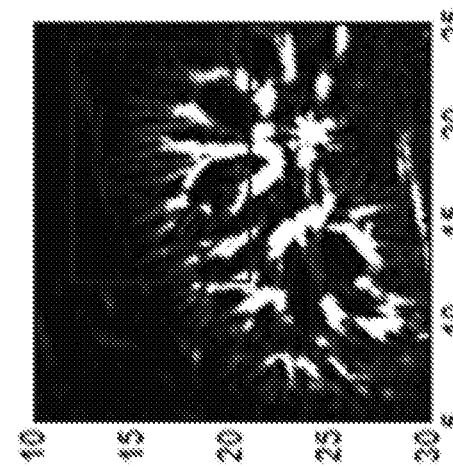
FIG. 7B: a background-free image after top-hat filtering.
Figure 7C:
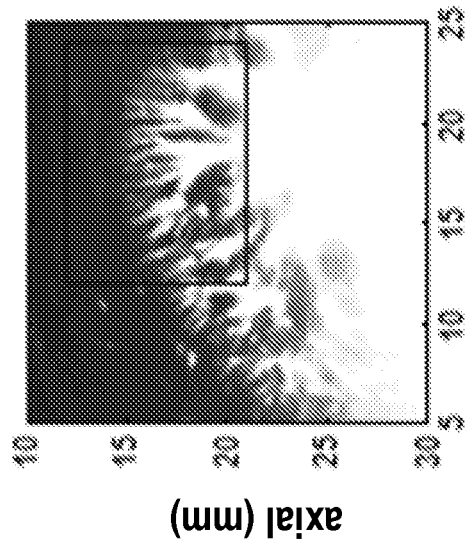
FIG. 7C: a final vessel image after vessel enhancement filtering.
Figure 7D:
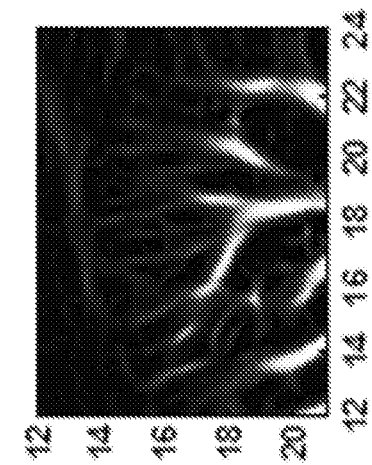
FIGS. 7D, 7E, and 7F present, on an enlarged scale, portions of images of FIGS. 7A, 7B, and 7C, respectively, outlined in such images with a rectangular box.
Figure 7E:
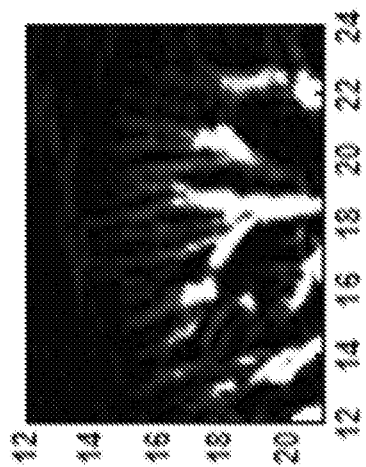
Figure 7F:

FIGS. 7A, 7B, and 7C provide images of the vasculature obtained after singular value thresholding (SVT) operation, the top-hat filtering (THF) operation, and the final image after vessel enhancement filtering (VEF), respectively. Again, it can be seen, that each processing stage results in an incremental improvement of the image quality, at least in terms of visibility of vasculature network. Each of FIGS. 7D, 7E, and 7E shows, on an expanded scale, a limited area that in the respectively-corresponding FIGS. 7A, 7B, and 7C is outlined with a rectangular box, to illustrated minute observable details of the small vessel structures. It can be noted that the application of VEF has considerably smoothened the walls in both small and large vessels without sacrificing the spatial resolution in identifying adjacent vessels.

Figure 14:
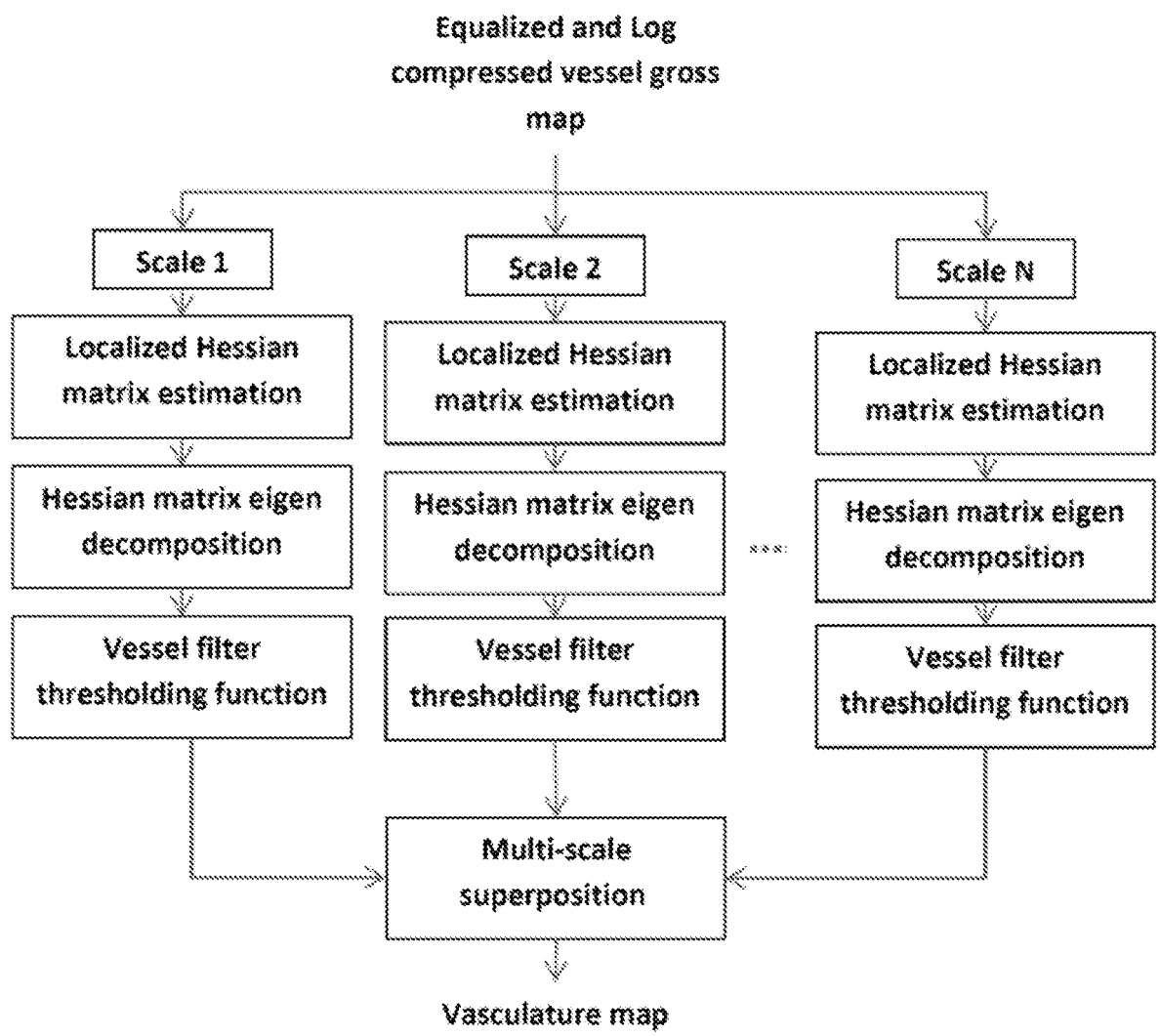
FIG. 14 presents a generalized block diagram of a multilevel vessel filtering process.

FIG. 14 presents a generalized block diagram of a multi-level vessel filtering process.

Quantitative Evaluation of Image Quality Improvements

Figure 8A:
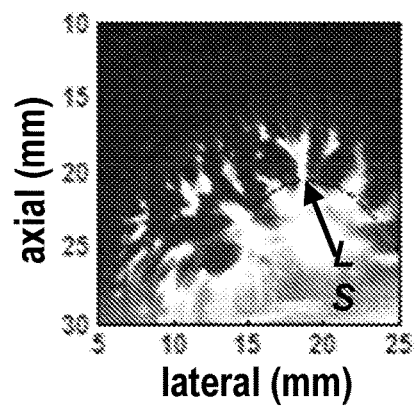
FIG. 8A: a representative line segment selected from an area with mostly large vessels overlaid on the vasculature image after singular value decomposition.
Figure 8B:
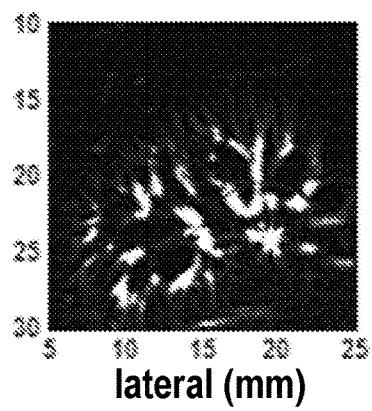
FIG. 8B: an image after top-hat filtering.
Figure 8C:
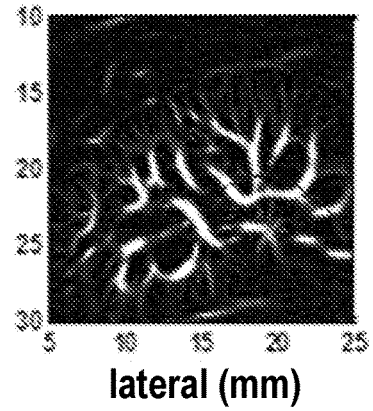
FIG. 8C: an image after vessel enhancement filtering.
Figure 8D:
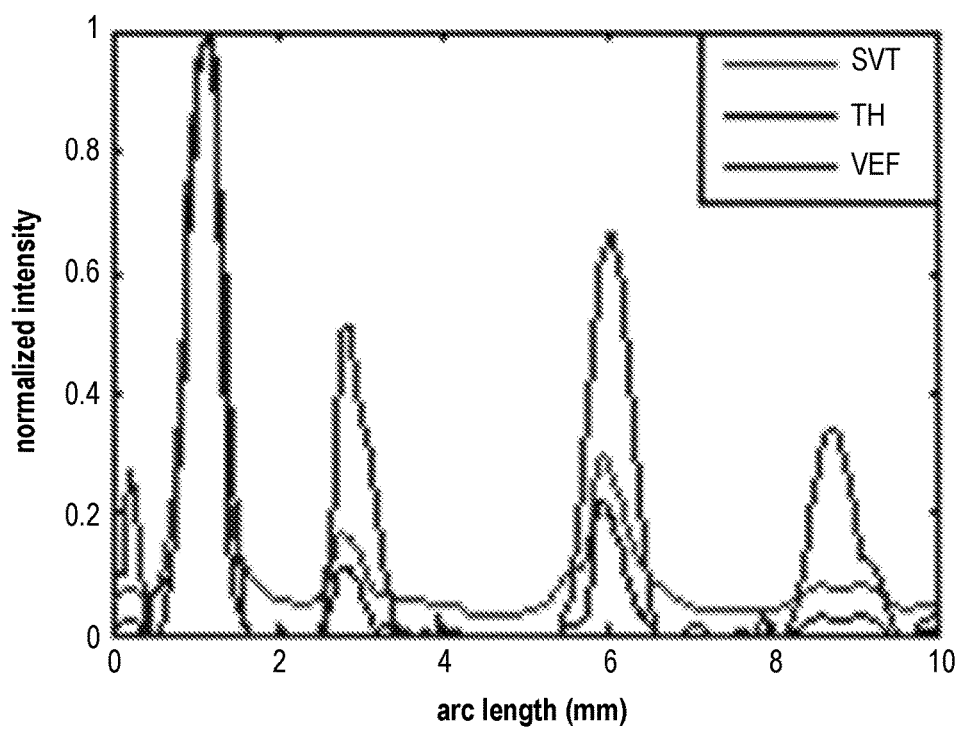
FIG. 8D: intensity curves along the line segment from each of images of FIGS. 8A, 8B, and 8C.

In order to obtain a quantitative, tangible measure of the gain or improvement in visualization achieved after each processing stage, a line segment from the intensity images acquired after each processing stage can be analyzed. To this end, FIGS. 8A, 8B, and 8C are presented with such line segment shown as LS in FIG. 8A and overlaid on the images obtained as a result of the SVT, THF and VEF processing, respectively. FIG. 8D is a plot of the normalized intensity variations along the line segment LS of each image. All plots are normalized to their corresponding maximum value. The line segment LS is seen to cross 4 vessels as seen in the VEF image (FIG. 8C), as well as in the line plot of FIG. 8D. (The latter illustrates intensity values along the line segment LS, from each of images of FIGS. 8A, 8B, 8C). It can be seen in FIG. 8B, that THF processing has considerably removed the background signal from the SVT image of FIG. 8A, so that vessels throughout the entire field of view are now observed with the use of a single dynamic range. Furthermore, the VEF processing has significantly amplified the intensity signals in the vessel regions. In order to better quantify these enhancements, the peak-to-side level (PSL) intensity for each vessel was assessed as, $$PSL = 20 \log_{10}\left(\frac{\Delta_{peak}}{\Delta_{side}}\right) (dB); \quad (14)$$

where $\Delta_{peak}$ is the image intensity of the brightest part of the visible vessel and $\Delta_{side}$ is the intensity at the darkest part of the image in the vicinity of the peak. The peak-to-side level was measured on the left (L-PSL) and right (R-PSL) sides of a vessel peak. For each vessel, the average peak-to-side level, $(PSL)^-$, was obtained as the average of L-PSL and R-PSL. These values are summarized in Table 1 of FIG. 8E. As it seen from this Table 1, both the THF and VEF filters are effective in removal of the side levels, which have resulted in a $(PSL)^-$ value of infinity for all vessels. The SVT method, on the other hand, shows bounded $(PSL)^-$ values, which translate into a background signal around the vessels.

Figure 9A:
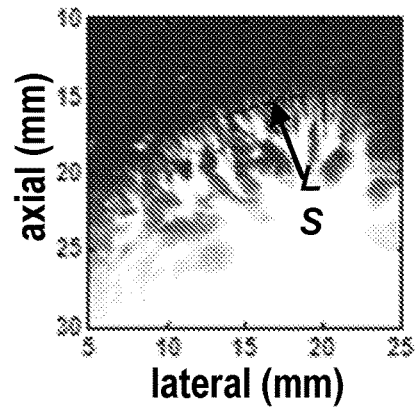
FIG. 9A: a representative line segment selected from an area with mostly small vessels overlaid on the vasculature image after singular value decomposition.
Figure 9B:
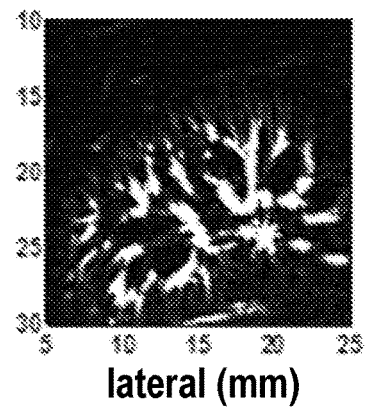
FIG. 9B: an image after top-hat filtering.
Figure 9C:
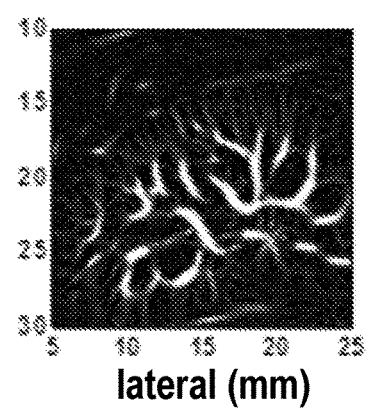
FIG. 9C: an image after vessel enhancement filtering.
Figure 9D:
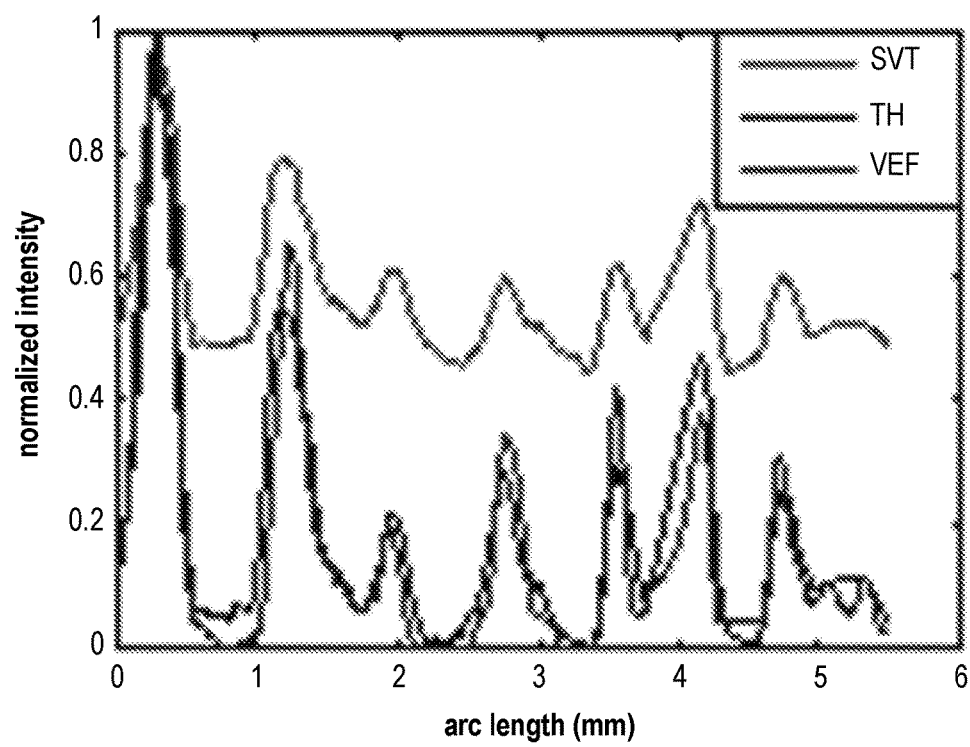
FIG. 9D: intensity curves along the line segment from each of images of FIGS. 9A, 9B, 9C.

Similarly, and in reference to FIGS. 9A, 9B, 9C, and 9D, a line segment LS was drawn across an area that contained mostly small vessels. The vessel maps for SVT-, THF- and VEF-filtered images with the overlaid segmented line are shown in FIG. 9A, 9B, 9C, respectively. The normalized intensity values from these segments are shown in FIG. 9D, where 7 vessels, which lay in the path of the line segment, can be identified. THF has effectively removed most of the background signal with minimal impact on the shape of the small vessels, FIG. 9B. Additionally, VEF, while preserving the vessel structures, has effectively suppressed the non-vessel regions, FIG. 9C. The average peak-to-side (PSLJ values are summarized in Table 2 of FIG. 9E. It can be observed that THF and VEF have consistently improved the $(PSL)^-$ values as compared to SVT. Additionally, the $(PSL)^-$ values corresponding to the post-VEF image processing are mostly larger than those of the image resulting from the THF-filtering. The minimum $(PSL)^-$ among all vessels was 4.01 dB, 14.17 dB and 37.19 dB (in SVT, THF and VEF images, respectively), evidencing the progressing improvement and sequential gain achieved after each processing step, thereby explaining the enhanced vessel visibility of the image of FIG. 9C.

Experimentally, all imaging steps were performed using an Alpinion Ecube12-R ultrasound machine (ALPINION Medical Systems, Seoul, Korea). In each study, raw in-phase and quadrature (IQ) data from 5 angle compounding plane wave imaging were acquired at 608 frames per second for a total duration of 3 seconds. The study of kidney and liver were performed on a healthy volunteer using a curved array, SC1-4H (ALPINION Medical Systems, Seoul, Korea) at 3 MHz. A linear array, L3-12H (ALPINION Medical Systems, Seoul, Korea) was used for studying one thyroid nodule and one breast lesion in two patients. Prior to our study, each patient signed an informed institutional review board (IRB) consent form. The SVT processing was performed based on the method described by C. Demené et al., in "Spatiotemporal Clutter Filtering of Ultrafast Ultrasound Data Highly Increases Doppler and fUltrasound Sensitivity," IEEE Transactions on Medical Imaging, vol. 34, pp. 2271-2285, 2015, the disclosure of which is incorporated by reference herein. The smallest singular value index for clutter removal, K, was set equal to 360, 200, 1200, 100 for kidney, liver, thyroid nodule and breast lesion respectively.

Additional Examples (In Vivo)

To provide evidence of the suitability of the proposed method for in vivo studies in different types of biological tissue organs, the following examples are presented based on the study of different organs (specifically, a thyroid nodule and a breast mass).

Hepatic Vasculature in Healthy Biological Tissue

Figure 10A:
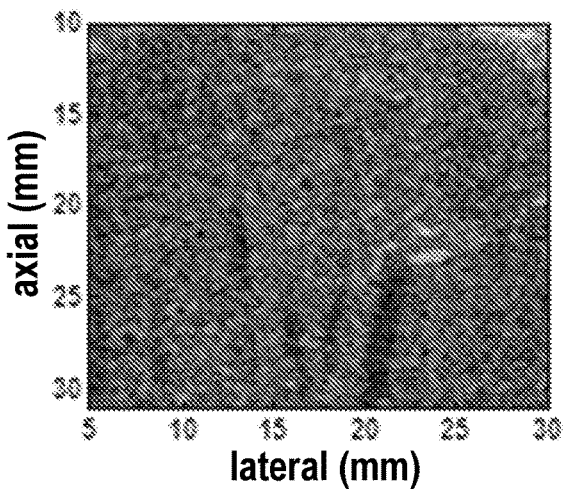
FIG. 10A: a B-mode image of hepatic vasculature network in the liver of a healthy volunteer.

The first example is that of the vasculature network in the healthy liver tissue. The B-mode image in FIG. 10A shows the reconstruction domain for the vasculature image. Given that liver is a highly perfused organ and that its vascularity is susceptible to change due to several conditions, the conventional Doppler imaging (which is usually used to monitor hemodynamic in hepatic vessels) is only capable of visualizing large arteries and veins in liver. These large vessels can be partially identified as tubular hypoechoic regions in FIG. 10A.

Figure 10B:
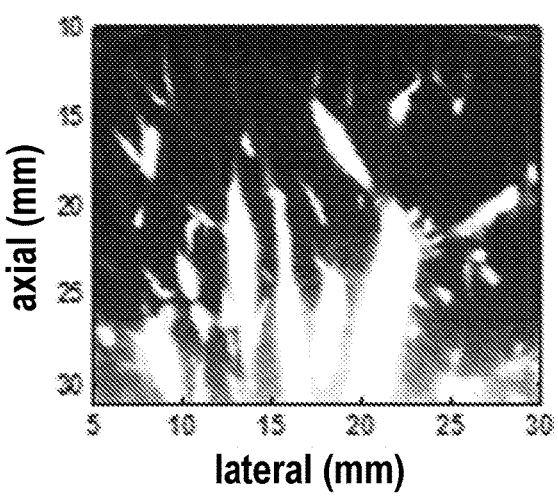
FIG. 10B: a gross image of the vessels using SVT.
Figure 10C:
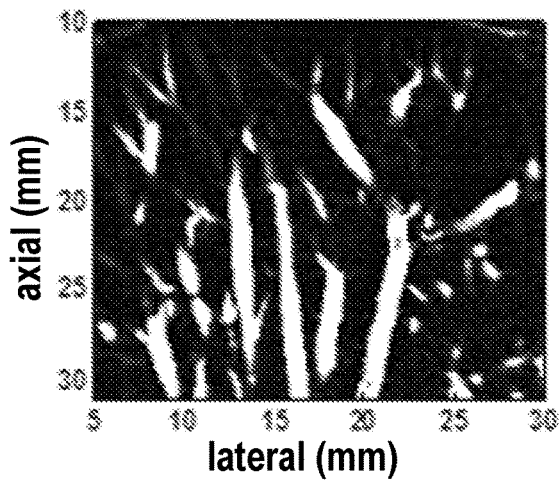
FIG. 10C: a vasculature image after background removal using THF.
Figure 10D:
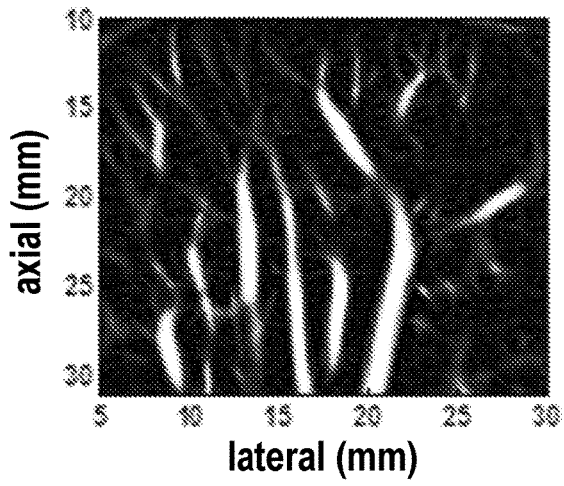
FIG. 10D: a final image of the hepatic vasculature network after VEF.

FIGS. 10B, 10C, and 10D show the SVT, THF and VEF images, respectively. It can be seen that intensity variations in the SVT image have limited the visibility of the entire vasculature network. The THF is effective in removal of most of the local and global background; hence vessels at different scales can be identified throughout the image of FIG. 10C. The VEF processing has further improved this vessel visibility through regularization of the vessels as tubular structures and suppression of the unstructured random background.

Malignant Thyroid Nodule

Figure 11A:
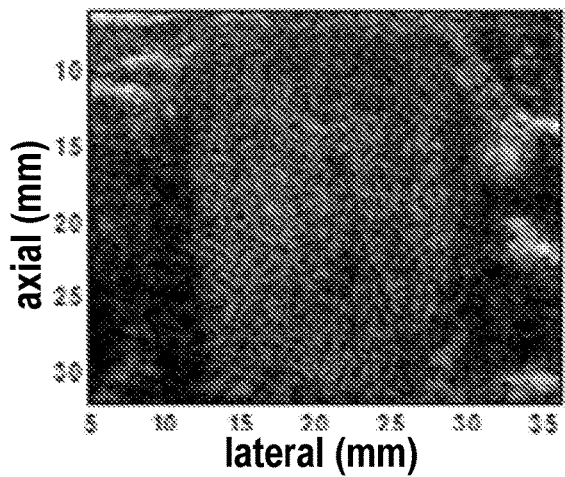
FIG. 11A: a B-mode image of a malignant thyroid papilloma identified between two vertical black columns.
Figure 11B:
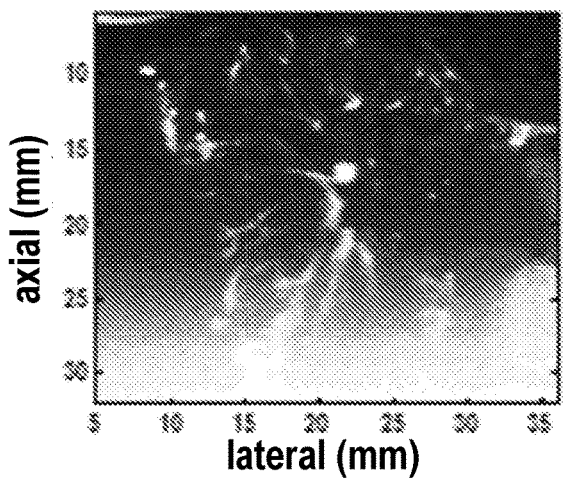
FIG. 11B: an image of the gross vasculature imaging inside the nodule using SVT.
Figure 11C:
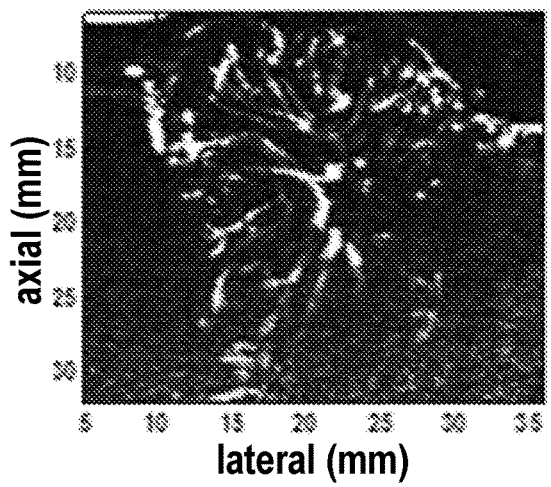
FIG. 11C: a vasculature image after background removal using THF.
Figure 11D:
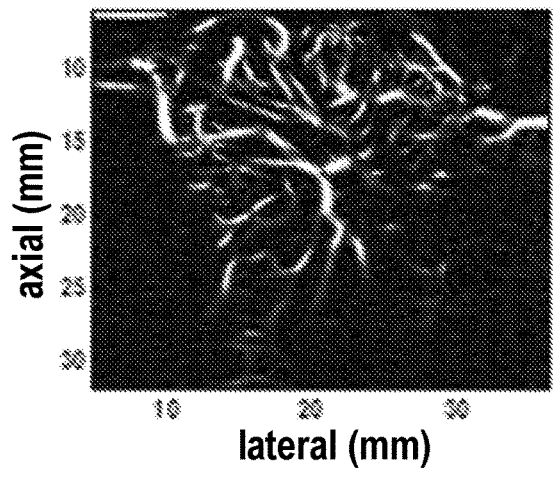
FIG. 11D: final image of the vasculature network inside the nodule after VEF.

The next example is the vasculature network in a human thyroid nodule. FIG. 11A presents the B-mode image of the nodule revealed by histology as a malignant papillary carcinoma. The nodule can be identified as the uniform scattering area with two shadowing columns on either side. FIGS. 11B, 11C, 11D show the vasculature image after SVT, THF and VEF, respectively. As can be observed in the SVT image, global and local intensity variations and a background signal have limited visibility of vessels throughout the image. FIG. 11C offers proof that the depth-dependent background signal was mostly removed by the THF filtering, with minimal impact on the vessel structures and morphology. The VEF processing significantly enhanced the vessel visibility and has effectively removed the residual background signal throughout the entire image (FIG. 11D). The connectivity of the vessels at different scales resembles a network with radial extension toward a small area which may indicate a high blood perfusion site in the nodule.

Benign Breast Lesion

Figures 12A, 12B, 12C, 12D:
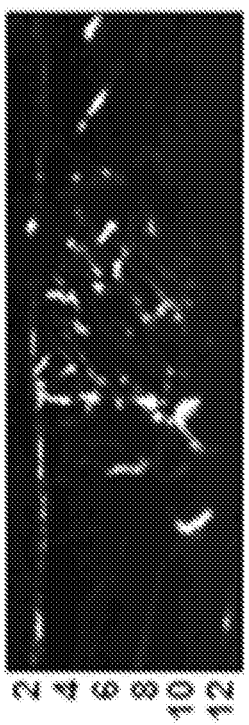
FIG. 12A: a B-mode image of a benign breast fibroadenoma identified as hypoechoic region with well-defined boundaries.
FIG. 12B: an image of the gross vasculature imaging inside the lesion using SVT.
FIG. 12C: a vasculature image after background removal using THF.
FIG. 12D: final image of the vasculature network inside the lesion after VEF.

To verify the suitability of the proposed method for imaging small vessels in breast lesions, an in vivo study in a patient with a benign fibroadenoma was additionally performed. The lesion can be identified in FIG. 12A as a well-circumscribed hypoechoic region. The gross image of the vascularity after SVT is shown in FIG. 12B. The THF and VEF images are shown in FIGS. 12C and 12D, respectively. The incremental enhancement after THF and VEF processes can be appreciated in terms of suppression of background signal and enhanced vessel visibility.

Overall it is appreciated, therefore, that the above-described approach effectuates the methodology of enhancement of visualization of the small vessels in power Doppler images obtained by singular value thresholding tissue clutter removal.

Using an ensemble of ultrasound raw data, blood flow activity may be further extracted from the raw ultrasound data using multi-dimensional processing. A gross network of microvasculature is obtained, but the image may not present clear visualization of the network due to background noise. The background noise, which may result from speckle redistribution and thermal noise from electrical devices, progressively increases with depth due to ultrasound signal attenuation, is estimated and removed from the image based on a mathematical morphology technique that can distinguish between fine blood structures and randomly distributed background noise. An equalization and logarithmic compression may then applied to bring the intensity level of different vessel sizes within the dynamic range of the image, regardless of morphological sizes of the image features. A multi-scale vessel filter may then be applied on the image to further extract blood vessels as tubular structures. The resulting image may be further enhanced using a multi-dimensional interpolation (such as, for example, cubic or spline interpolation).

The final images are able to present detailed maps of tissue vasculature network in micron-levels which can be many centimeters deep into tissue. This approach provides unprecedented visualization and high resolution of tissue microvasculature well beyond the capabilities of existing Doppler methods. The proposed approach is noninvasive and does not require any contrast enhancing agent.

Figure 13A:
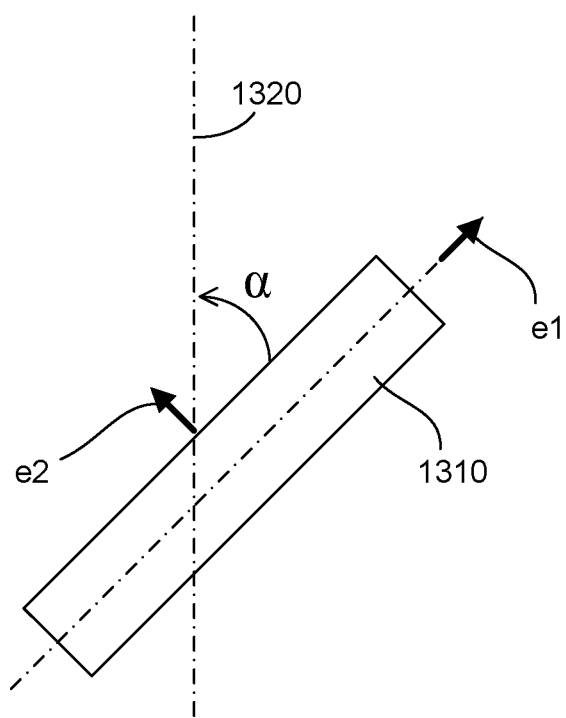
FIG. 13A provides illustration to orientation of a blood vessel with respect to the ultrasound beam.

If desired, the final microvasculature image can be superimposed as a color overlay on the initial B-mode image, and/or displayed alongside the B-mode image to facilitate fine anatomy comparison for diagnostic purposes. Specifically, in one embodiment the clutter-free spatial/temporal data can be further used to estimate Doppler shift due to blood flow at each pixel within the imaging plane. Temporal data are transformed into Fourier domain and effective Doppler shift is assessed using the center-of-mass approach based on, $$f_{Doppler}(m, n) = \frac{\int f|S(f)|^2 df}{|S(f)|^2}; \quad (15)$$

where S (f) is a double-sided Fourier spectrum of the time data at each pixel. The Doppler shift creates a 2D (or 3D, depending on the embodiment) color flow speed mask, $$CFM(m, n) = \frac{f_{Doppler}(m, n)}{f \cos(\alpha)} c; \quad (16)$$

where c is the speed of sound, f is the center frequency of the transmitted ultrasound pulse, and $\alpha$ is the angle describing the orientation of the blood vessel, 1310, with respect to the axis, 1320 of propagation of the ultrasound beam. See FIG. 13A, in which $e_1$ and $e_2$ are the eigenvectors corresponding to the eigenvalues $\lambda_1$ and $\lambda_2$ such that $|\lambda_2|>|\lambda_1|$ (see Eqn. (11)).

Once the CFM map is calculated for each pixel, the final CFI map is calculated as, $$CFI = CFM \cdot \Lambda \quad (17).$$

Figure 13B:
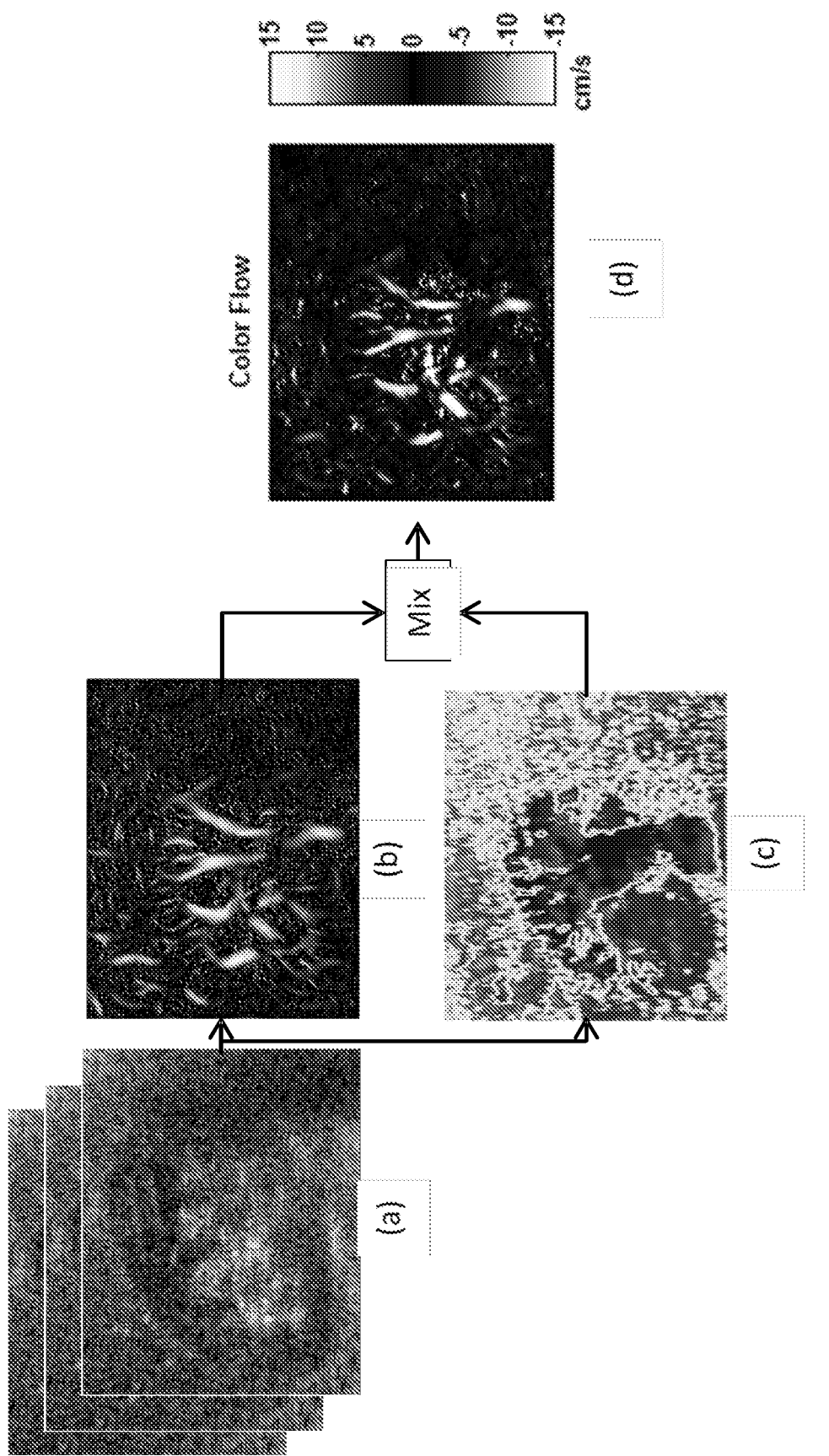
FIG. 13B: (a) Sequence of high frame rate ultrasound data of a kidney in a healthy volunteer (b) tissue clutter-free microvasculature network (c) color flow mask (d) final color flow map with blood flow speed estimation.

The resulting CFI map can be displayed as a separate map or be overlaid over a corresponding B-mode image. See FIG. 13B.

Furthermore, the spatial-temporal data can be further binned in overlapping windows along the time axis. A spectrogram of the data is then calculated along the time axis and the processing of Eqns. (15)-(16) is repeated for data in each time bin. The resulting sequence of CFI frames is then created and recorded to form continuous color flow imaging (CCFI).

Furthermore, the Doppler data from each time bin in the above-discussed CCFI can be modulated on a single carrier tone to produce an audible continuous signal ("audio Doppler capability"). In one implementation, an audibly-perceived Doppler signal representing microvasculature targets at depths of many centimeters was recorded, evidencing the depth-penetration capability of the described methodology.

Artifact and Noise Suppression Via Spectral Subtraction

Tissue motion relative to the ultrasound beam is a limiting factor in performance of ultrasound clutter removal methods. Singular value thresholding can handle motions that are coaxial with the ultrasound beam as they result in low rank processes. Lateral motions, especially from highly echogenic tissue areas, are hard to remove using SVD. As a result, tissue clutter residue can remain after singular value thresholding.

Figure 15:
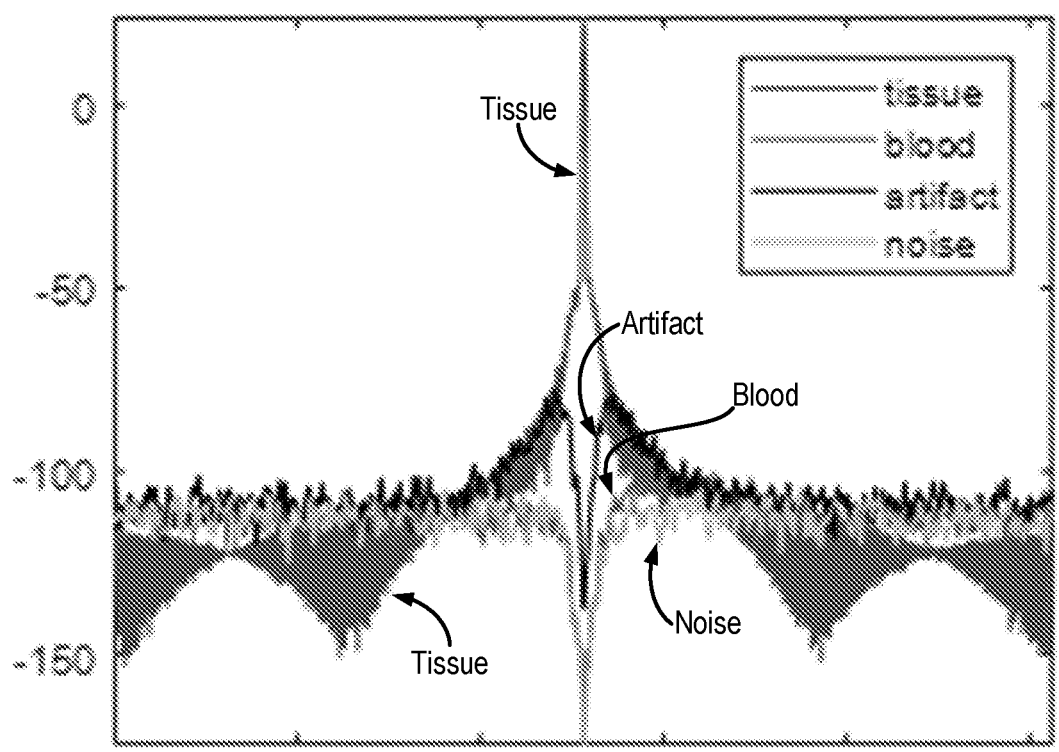
FIG. 15 is an example of spectral features of tissue clutter (blue), tissue clutter residue artifact after SVD (black), blood (red), and noise (green).

The methods described in the present disclosure can be implemented to mitigate these effects based on spectral features of tissue clutter residue and noise after SVD. FIG. 15 shows an example of the spectral representation of the artifact, blood, and noise from an in vivo study.

The method utilizes the spectral symmetry of the tissue clutter artifact to suppress any signals with symmetric spectrum. Beside blood signal, which presents mostly unilateral spectrum, the artifact and noise signals present symmetric Fourier spectra. These features can be verified in the example shown in FIG. 15.

Assume $x_{SVD}(r,t)$ is the signal after SVD clutter removal. In the old method, the power Doppler-like vasculature image, I, would be formed as, $$I = \frac{1}{T} \int |x_{SVD}(r, t)|^2 dt. \tag{18}$$

Based on the methods described in the present disclosure and using Parseval's theorem, Eqn. (18) can be modified as, $$I = \text{abs}(I_1 - I_2); \tag{19}$$

$$I_1 = \frac{1}{2T} \int |X_{SVD}(r, f)|^2 (1 + \text{sign}(f)) df; \tag{20}$$

$$I_2 = \frac{1}{2T} \int |X_{SVD}(r, f)|^2 (1 - \text{sign}(f)) df. \tag{21}$$

Where $X_{SVD}(r,f)$ is the Fourier spectra computed as the Fourier transform of $x_{SVD}(r,t)$.

Figure 16:
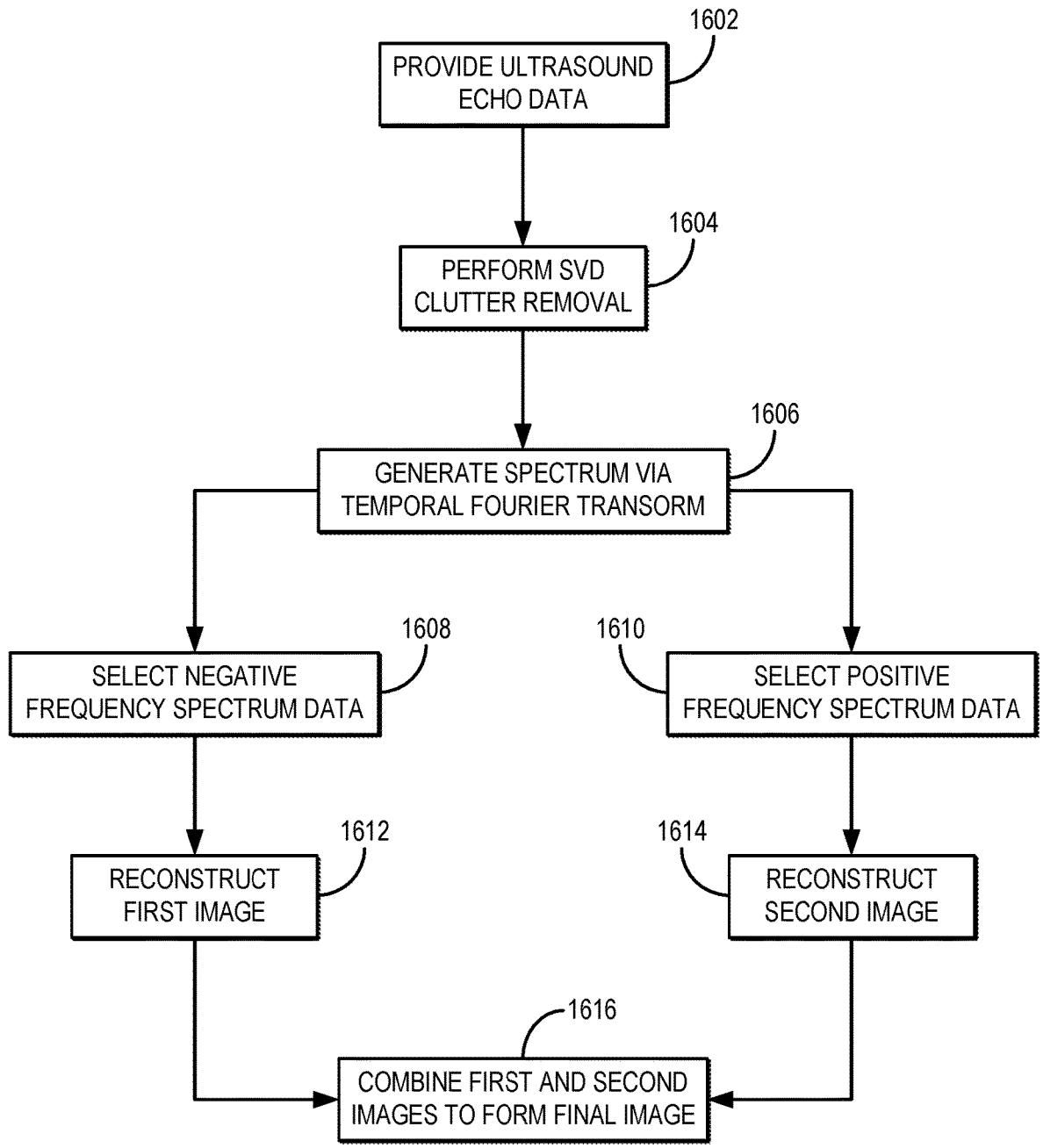
FIG. 16 is a flowchart setting forth the steps of an example method for reducing artifacts and noise in a tissue microvasculature image using a spectral subtraction technique.

Referring now to FIG. 16, a flowchart is illustrated as setting forth the steps of an example method for producing an image with reduced artifacts and noise. The method includes providing ultrasound echo data to a computer system, as indicated at step 1602. The ultrasound echo data may be provided to the computer system by retrieving previously acquired data from a memory or other data storage. The ultrasound echo data may also be provided to the computer system by acquiring the data with an ultrasound system and communicating the data to the computer system, which may form a part of the ultrasound system itself.

The ultrasound echo data are then processed using a clutter removal technique, such as an SVD-based clutter removal technique, as indicated at step 1604. As one example, the methods described in the present disclosure can be used to implement the clutter removal. In some implementations, a regular SVD can be used. In other implementations, a generalized SVD can be implemented.

A Fourier spectrum is generated by performing a temporal Fourier transform, as indicated at step 1606. The negative frequency components of the Fourier spectrum are selected and stored as negative frequency spectrum data at step 1608, and the positive frequency components of the Fourier spectrum are selected and stored as positive frequency spectrum data at step 1610. From the negative frequency spectrum data, a first image is reconstructed, as indicated at step 1612. From the positive frequency spectrum data, a second image is reconstructed, as indicated at step 1614. As one example, the first image can be reconstructed using Eqn. (20) and the second image can be reconstructed using Eqn. (21). The steps of selecting the positive and negative spectrum data and reconstructing first and second images can be performed in parallel processing, as shown in FIG. 16, or can be performed sequentially. In the latter case, it will be appreciated that the first image can be reconstructed before the second image, or vice versa.

Using the first image and the second image, a final image in which artifacts and noise are reduced is generated, as indicated at step 1616. In some instances, the final image is produced by computing a difference between the first image and the second image. In other implementations, the final image can be produced based on an estimation method using the first and second images, which can avoid enhancing noise variance.

Post-SVD Motion Compensation for Coherent Ultrasound Power Doppler Integration in Microvasculature Imaging Singular value thresholding has emerged as a powerful tool in removing strong clutter signals from weak red blood cell echoes; even in the presence of strong bandwidth overlap due to tissue motion. In spite of this powerful signal separation, the recovered blood echoes can still inherit the global misregistration imposed by tissue motion. Hence, under severe motions power Doppler images can present a ghost artifact that might lead to blurred appearance of the detected vessels and inaccurate morphological features, such as diameter. It is an aspect of the present disclosure to provide for using rank analysis over classic frequency filtering in separating weak blood echoes embedded in moving tissue. It is another aspect of the present disclosure to implement a motion compensation algorithm that is directly implemented in the blood echoes recovered via singular value thresholding. These methods provide significant image stabilization in the final power Doppler images compared to singular value thresholding alone.

Ultrafast ultrasound plane wave imaging with multiple angle compounding has enabled acquiring data from large fields of view at high frame rates. The high degree of spatial and temporal coherence provided by this imaging method has been advantageous for extending clutter removal capabilities and enabling imaging small vessels.

The phase of ultrasound radiofrequency (or I-Q) data is highly sensitive to subtle motions, such that slight rearrangement of scatterers caused by motions can create a Doppler shift. In mostly stationary tissue, the observed shift can generally be attributed to red blood cells, which are the main scatterers in blood. Hence, a high-pass filter can effectively seprate the blood signals from tissue components. In the presence of tissue motion, however, Doppler shifts can be present in both tissue signals and blood signals. Hence, the success of frequency domain clutter removal is dependent on the amount of Fourier spectral overlap between tissue and blood signals, such that small vessels are usually masked. In order to enable small vessel imaging, it is natural to search for other transformation (or decomposition) domains that can be used to better search for other characteristics.

In contrast to blood motion, which is governed by equations of fluid, tissue motions and deformations are mostly governed by the equations of incompressible deformable solid. Hence, instead of sporadic scatter motions present in blood vessels, tissue scatterers move coherently, such that their echo signature creates a low rank process if imaged in time. As a result, a rank analysis, tissue-blood signal separation might be possible even in the case of strong bandwidth overlap. Even though SVD can significantly extend the domain for separation of blood and tissue components, the recovered blood data still inherit the same transformational motion imposed by tissue which will undermine the quality of power Doppler images due to incoherent integration.

Thus, it is an aspect of the present disclosure that signal separation via low rank approximation can be implemented for its utility in clutter removal for imaging small vessels. A motion compensation algorithm that provides coherent integration of post-SVD ensembles for formation of power Doppler-like images is also implemented.

Clutter Removal Via Frequency Selective Filtering

For 2-D ultrasound imaging, the beam-formed data can be represented as, $$s(r,\tau) = s_c(r,\tau) + s_b(r,\tau) + w(r,\tau) \quad (22);$$

where $s_c(r,\tau)$, $s_b(r,\tau)$ and $w(r,\tau)$ are the tissue, blood and noise signals at location $r$ and slow time $\tau$ respectively. Assuming linearity, Eqn. (22) can be written as, $$s(r,\tau) = \sum_{i=1}^{N_c} p(r) *_r c_i(r,\tau) + \sum_{i=1}^{N_b} p(r) *_r b_i(r,\tau) + w(r,\tau); \quad (23)$$

where $p(r)$ is the spatially-invariant imaging point spread function, $*_r$ is the spatial convolution operation, and $c_i(r,\tau)$ and $b_i(r,\tau)$ are tissue and blood complex reflectivity coefficients respectively. Using a narrowband approximation, in presence of tissue motion and blood activity, $$s(r,\tau) = \quad (24)$$

$$\sum_{i=1}^{N_c} p(r-r_i)c_i(\tau)e^{j(\phi_i^c - \frac{2\pi}{\lambda}v^c\tau)} + \sum_{i=1}^{N_b} p(r-r_i)b_i(\tau)e^{j(\phi_i^b - \frac{2\pi}{\lambda}(v_i^b\tau + v^c\tau))} +$$

$$w(r,\tau)e^{-j\frac{2\pi}{\lambda}v^c\tau}\sum_{i=1}^{N_c} c_i(\tau)p(r-r_i)e^{j\phi_i^c} +$$

$$\sum_{i=1}^{N_b} b_i(\tau)p(r-r_i)e^{j(\phi_i^b - \frac{2\pi}{\lambda}(v_i^b\tau + v^c\tau))} + w(r,\tau);$$

where $\lambda$ is the imaging wavelength and $\varphi_i^c$ and $\varphi_i^b$ are the arbitrary phases for $i^{th}$ tissue and blood scatterer respectively and $c_i(\tau)$ and $b_i(\tau)$ are slowly varying processes representing local tissue and blood scattering variations over time. Hence, in the Fourier spectral domain, $$S(r,f) \approx P_c\left(r, f - \frac{v^c}{\lambda}\right) + P_b\left(r, f - \frac{v^c}{\lambda} - \frac{\overline{v^b}}{\lambda}\right) + W(r,f); \quad (25)$$

where $P_c$ and $P_b$ are the power spectral densities of the tissue and blood components respectively. Hence the Doppler shift associated with the tissue motion is $$\frac{v^c}{\lambda}$$

and the average Doppler shift due to blood activity and tissue motion is $$\frac{v^c}{\lambda} + \frac{\overline{v^b}}{\lambda}. \text{ If } \frac{v^c}{\lambda} + \frac{\overline{v^b}}{\lambda} \gg \frac{v^c}{\lambda},$$

a high-pass clutter filter can effectively remove the tissue signal, leaving mostly blood signature and noise at the output. However, when significant bandwidth overlap exits (e.g. slow blood flow or rapid tissue motions), frequency selective filtering is no longer effective.

Clutter Removal Via Low Rank Approximation

The coherent motion resulting from tissue motion generates a spatial-temporal process which is low rank. This mainly stems from the fact that tissue behaves like a deformable solid, such that arbitrary motions are not allowed. On the other hand, blood activity and noise generate processes that cannot be modeled low rank. This provides a sub-space framework for which, even in highly moving tissues, clutter signal can be removed as the low rank sub-space of a spatial-temporal matrix. To elaborate, consider the signal representation in Eqn. (24). The discretized spatial-temporal equivalent of this equation can be formed as, $$S = P_c + P_b + W = pe^H + P_b + W; \text{ where,} \quad (26)$$

$$p = \begin{bmatrix} c_1 p((n - r_1)\Delta r)e^{j\phi_1^c} \\ c_1 p((n - r_2)\Delta r)e^{j\phi_2^c} \\ \vdots \\ c_1 p((n - r_M)\Delta r)e^{j\phi_M^c} \end{bmatrix}; \quad (27)$$

$$e = \begin{bmatrix} 1 \\ e^{-j\frac{2\pi}{\lambda}v^c T_s} \\ \vdots \\ e^{-j\frac{2\pi}{\lambda}v^c(N-1)T_s} \end{bmatrix}; \quad (28)$$

and $P_b$ and $W$ are blood and noise signals sampled in space and time.

The matrix representation in Eqn. (26) is composed of a rank-one part due to tissue signal and two additional terms $P_b$ and $W$, which represent blood and noise signals respectively. Using this formulation, and ignoring the noise, the blood signal can be well approximated as an intermediate subspace of the vector space spanned by S as, $$P_b \approx \sum_{2}^{k_{max}} \lambda_i u_i v_i^H; \quad (29)$$

where $S=U\Lambda V^H$ is the singular value decomposition (SVD) of S and $U=[u_1, u_2, \ldots, u_s]$ and $V=[v_1, v_2, \ldots, v_s]$ are unitary matrices, and $\Lambda=\text{diag}(\lambda_1, \lambda_2, \ldots, \lambda_r)$ is a diagonal matrix of singular values and $k_{max}$ is the maximum rank of the blood-related signals. In this derivation, no assumption was made about tissue velocity $v^c$ and hence its induced Doppler shift. Hence, in an ideal situation where all tissue components move perfectly coherently, the performance of SVD clutter removal is independent of motion speed as tissue contribution can be always approximated as a rank-one process. While this approach highlights the additional capability that low rank approximation provide for clutter removal, it is far from reality. In practice, tissue motion presents some degree of variations due to natural heterogeneity of tissue structural properties. Hence, in decomposition of the spatial-temporal matrix S, tissue occupies the lowest rank sub-space as $P_c = \Sigma_1^{K_1} \lambda_i u_i v_i^H$ and blood signal can be approximated as an intermediate sub-space as, $$P_b \approx \sum_{k_1+1}^{k_{max}} \lambda_i u_i v_i^H. \tag{30}$$

Coherent Image Formation Using Non-Rigid Registration

Even though SVD provides robust signal separation, even in presence of bandwidth overlap, the recovered blood signals based on Eqns. (29), (30) still present the same global spatial variations imposed by tissue motion. Hence if not corrected, the final image may present a blurring effect.

Hence, in order to recover the true spatial distribution of blood dynamics, tissue-induced motions should be corrected. In the case of forming power Doppler images, this motion compensation provides coherent power integration, which in turn improves vessel visibility and removed the blurring artifact.

As one example, global time-delay estimation in ultrasound elastography ("GLUE") can be used estimation of two-dimensional non-rigid displacements. The displacement between is calculated for all imaging frames compared to the first frame, such that a Lagrangian estimate of tissue (and hence blood vessels) is obtained. This displacement field is then used to remove motion from SVD filtered data $P_b$ in Eqn. (30).

Figure 17:
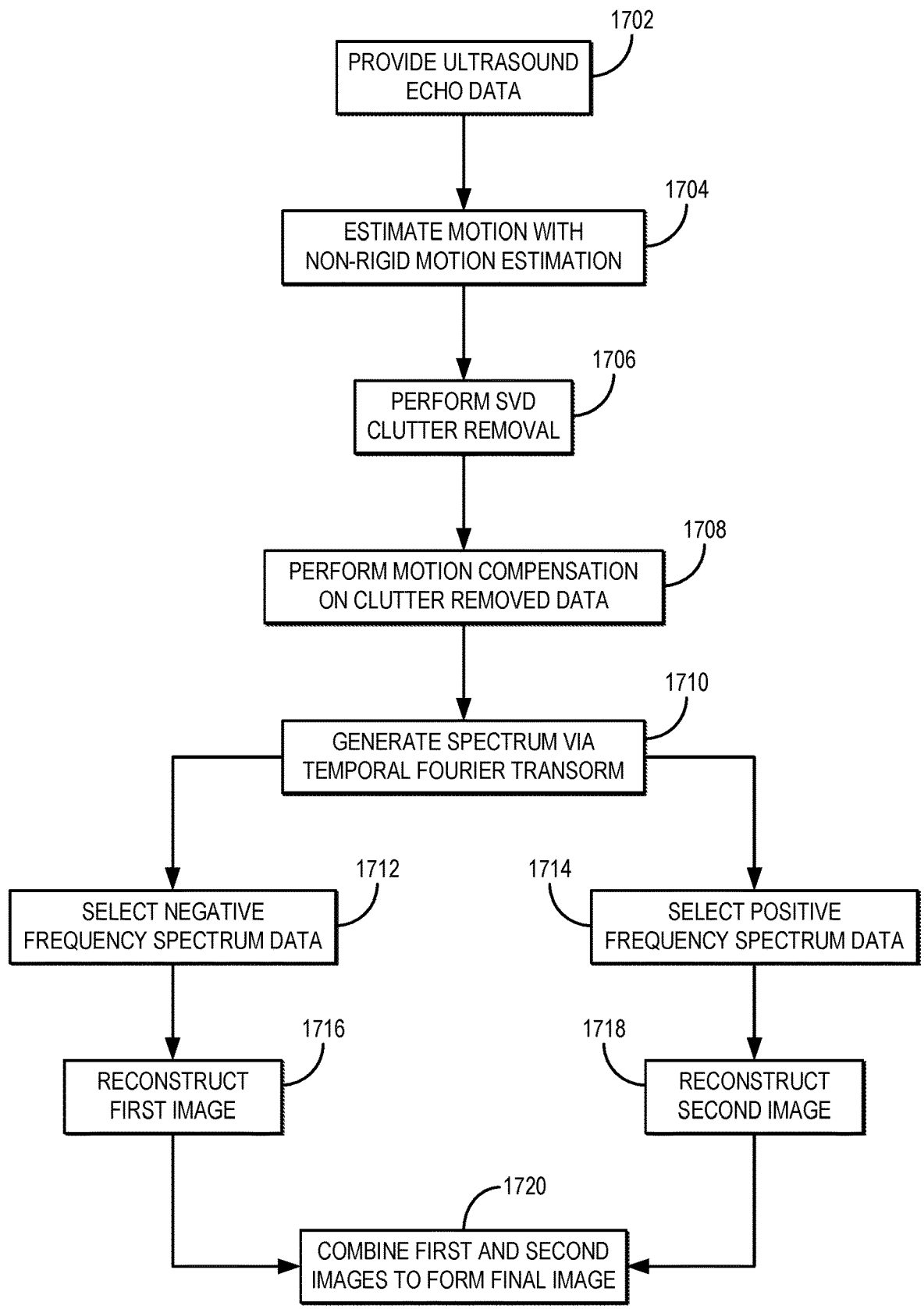
FIG. 17 is a flowchart setting forth the steps of an example method for reducing artifacts and noise in a tissue microvasculature image using a spectral subtraction technique with motion compensation to reduce motion-related blurring and artifacts.

Referring now to FIG. 17, a flowchart is illustrated as setting forth the steps of an example method for producing a motion-compensated image with reduced artifacts and noise. The method includes providing ultrasound echo data to a computer system, as indicated at step 1702. The ultrasound echo data may be provided to the computer system by retrieving previously acquired data from a memory or other data storage. The ultrasound echo data may also be provided to the computer system by acquiring the data with an ultrasound system and communicating the data to the computer system, which may form a part of the ultrasound system itself.

Motion data are then estimated using a non-rigid motion estimation, as indicated at step 1704. As mentioned above, in some implementations the motion data can be estimated using global time-delay estimation in ultrasound elastography. The motion data are used to provide motion compensation.

The ultrasound echo data are then processed using a clutter removal technique, such as an SVD-based clutter removal technique, as indicated at step 1706. As one example, the methods described in the present disclosure can be used to implement the clutter removal. In some implementations, a regular SVD can be used. In other implementations, a generalized SVD can be implemented.

Motion compensation can then be performed on the clutter removed data, as indicated at step 1708. In some other implementations, the motion compensation can be performed on the ultrasound echo data, and then clutter removal can be performed on the motion-compensated ultrasound echo data. In these instances, interpolation error may change the singular value decay behavior and consequently affect the performance of SVD clutter removal.

In any instance, spectrum data are next generated by performing a temporal Fourier transform on the clutter removed data, as indicated at step 1710. The negative frequency components of the Fourier spectrum are selected and stored as negative frequency spectrum data at step 1712, and the positive frequency components of the Fourier spectrum are selected and stored as positive frequency spectrum data at step 1714. From the negative frequency spectrum data, a first image is reconstructed, as indicated at step 1716. From the positive frequency spectrum data, a second image is reconstructed, as indicated at step 1718. As one example, the first image can be reconstructed using Eqn. (20) and the second image can be reconstructed using Eqn. (21). The steps of selecting the positive and negative spectrum data and reconstructing first and second images can be performed in parallel processing, as shown in FIG. 17, or can be performed sequentially. In the latter case, it will be appreciated that the first image can be reconstructed before the second image, or vice versa.

Using the first image and the second image, a final image in which artifacts and noise are reduced is generated, as indicated at step 1720. In some instances, the final image is produced by computing a difference between the first image and the second image. In other implementations, the final image can be produced based on an estimation method using the first and second images, which can avoid enhancing noise variance.

All these advantages of the proposed methodology clearly facilitate the adaptation of the proposed imaging method into routine clinical work-ups to provide clinically-relevant information concerning different disease and conditions that cause alterations in the tissue vascularity. The proposed method benefits from all the advantages of ultrasound including: safety, low cost and ease of operation.

The present disclosure has described one or more preferred embodiments, and it should be appreciated that many equivalents, alternatives, variations, and modifications, aside from those expressly stated, are possible and within the scope of the invention.

The invention claimed is:

1. A method for generating an image depicting tissue microvasculature using an ultrasound system, the steps of the method comprising:
   (a) with an ultrasound imaging system, recording a sequence of first images of a blood vessel of a tissue, said blood vessel having a first spatial scale;
   (b) transforming the sequence of first images into a second image by separating a weakly-correlated ultrasound data of the sequence of first images from a highly-correlated ultrasound data of the sequence of first images, wherein said separating is carried out based on a pre-determined threshold value, wherein said weakly-correlated ultrasound data represents blood activity, wherein said highly-correlated ultrasound data represents more than 99% of energy in singular values;

(c) generating a third image by reducing a spatially-variant background signal corresponding to features having a second spatial scale from the second image using a circular morphology structure, wherein the spatially-variant background signal is reduced by at least 10 dB;

(d) transforming the third image into a fourth image by equalizing variations of intensity across the third image to compensate for ultrasound fluctuations caused by relative orientation of a probe of the ultrasound imaging system and the blood vessel; and (e) adjusting visibility of said blood vessel presented for viewing while forming a visually-perceived output, from said ultrasound imaging system, in which the third image has been modified based on representation of said blood vessel as a tubular structure.

2. The method according to claim 1, wherein said recording includes recording the sequence of first multiple image frames at a rate of at least 100 frames per second, said multiple image frames containing data in a form of at least one of (i) in-phase and quadrature (IQ) data and (ii) radiofrequency (RF) data.

3. The method according to claim 1, wherein said separating is carried out based on the threshold value determined using an energy-decay rate in an eigenspace spectral domain.

4. The method according to claim 1, wherein said transforming the third image includes at least one of (i) equalizing variation of the intensity across the third image to compensate for depth-dependent attenuation in said tissue, and (ii) equalizing variation of the intensity across the third image to compensate for partial visibility of the blood vessel caused by limited elevational thickness thereof.

5. The method according to claim 1, wherein said adjusting includes using Hessian-based filtering of an image feature.

6. The method according to claim 5, further comprising removing background information from the third image using morphology filtering prior to said using the Hessian-based filtering.

7. The method according to claim 1, wherein said transforming the third image includes forming said fourth image in which, as a result of said equalizing variations, contrast of the blood vessel is increased within a constant dynamic range.

8. The method according to claim 1, wherein the first spatial scale represents sub-millimeter dimensions, and dimensions represented by the second spatial scale are larger than those of the first spatial scale.

9. The method according to claim 1, wherein said transforming the sequence of first images includes using one of:
singular value thresholding;
a multi-resolution processing algorithm; and
a blind source separation algorithm.

10. The method according to claim 1, further comprising comparing the first image with said visually-perceived output by displaying the first image while forming said visually-perceived output as a color overlay on the first image, to characterize anatomy of said tissue and to generate a visually-perceived identification, in said color overlay, of different regions of tissue possessing vascularity features that are absent in a conventionally-acquired ultrasound B-mode image of said tissue.

11. The method according to claim 10, further comprising displaying indicia of a visually-enhanced boundary of a highly-perfused lesion based on density of blood-vessels in said tissue.

12. The method according to claim 1, further comprising comparing at least one of a first image and the second image with said visually-perceived output by displaying said at least one of the first and second images and the visually-perceived output side-by-side to spatially correlate pattern of microvasculature in the tissue with relevant anatomy thereof.

13. The method according to claim 1, wherein said transforming the third image includes comprising applying logarithmic compression to imaging data to equalize intensity values of pixels across the third image regardless of morphological sizes of image features and to increase a dynamic range of the third image.

14. The method according to claim 1, wherein said recording, said transforming the sequence of first images, said generating, and said transforming the third image includes processing a three-dimensional (3D) ultrasound image to extract and display a 3D structure of a vessel tree of said tissue.

15. The method according to claim 1, devoid of administering a contrast-enhancing agent to the tissue.

* * * * *

UNITED STATES PATENT AND TRADEMARK OFFICE
CERTIFICATE OF CORRECTION

PATENT NO. : 11,213,278 B2
APPLICATION NO. : 16/614474
DATED : January 4, 2022
INVENTOR(S) : Azra Alizad et al.

It is certified that error appears in the above-identified patent and that said Letters Patent is hereby corrected as shown below:

In the Specification

Column 1, Line 43, "low cluttered" should be --low resolution and weak performance when highly spatially-cluttered--.

Column 9, Line 29, Eq. (1), "$r(z,t) = e^{-\alpha z}s_c(z,t0 + e^{-\alpha z}s_b(z,t) + n(t)$" should be --$r(z,t) = e^{-\alpha z}s_c(z,t) + e^{-\alpha z}s_b(z,t) + n(t)$--.

Column 11, Line 52, "Sr" should be --$\delta r$--.

Column 14, Line 16, "(PSLJ"" should be --$(PSL)^-$--.

Signed and Sealed this
Seventeenth Day of May, 2022

Katherine Kelly Vidal
*Director of the United States Patent and Trademark Office*